US008318805B2

(12) United States Patent
Messadek

(10) Patent No.: US 8,318,805 B2
(45) Date of Patent: *Nov. 27, 2012

(54) MODULATION OF NITRIC OXIDE SYNTHASES BY BETAINES

(76) Inventor: Jallal Messadek, Liege (BE)

( * ) Notice: Subject to any disclaimer, the term of this patent is extended or adjusted under 35 U.S.C. 154(b) by 251 days.

This patent is subject to a terminal disclaimer.

(21) Appl. No.: 11/747,167

(22) Filed: May 10, 2007

(65) Prior Publication Data

US 2007/0213399 A1 Sep. 13, 2007
US 2010/0305206 A9 Dec. 2, 2010

Related U.S. Application Data

(63) Continuation-in-part of application No. PCT/BE2005/000161, filed on Nov. 9, 2005.

(30) Foreign Application Priority Data

Nov. 10, 2004 (WO) ................ PCT/BE2004/000163
Jan. 19, 2005 (WO) ................ PCT/BE2005/000006

(51) Int. Cl.
*A61K 31/205* (2006.01)
(52) U.S. Cl. ........................................ 514/556; 514/561
(58) Field of Classification Search .................. None
See application file for complete search history.

(56) References Cited

U.S. PATENT DOCUMENTS

| | | | |
|---|---|---|---|
| 3,577,534 A | 5/1971 | Koh et al. | |
| 4,066,756 A | 1/1978 | Orr et al. | |
| 4,140,755 A | 2/1979 | Sheth et al. | |
| 4,605,548 A | 8/1986 | Ushiyama et al. | |
| 4,703,045 A | 10/1987 | Guinot | |
| 4,814,179 A | 3/1989 | Bolton | |
| 4,902,718 A * | 2/1990 | Bayless et al. ................ | 514/562 |
| 4,911,916 A | 3/1990 | Cleary | |
| 4,968,719 A | 11/1990 | Brevetti | |
| 5,217,997 A * | 6/1993 | Levere et al. ................. | 514/565 |
| 5,342,621 A | 8/1994 | Eury | |
| 5,405,614 A | 4/1995 | D'Angelo et al. | |
| 5,716,941 A | 2/1998 | Rabinoff | |
| 5,814,599 A | 9/1998 | Mitragotri et al. | |
| 5,876,780 A | 3/1999 | Virtanen et al. | |
| 5,880,098 A | 3/1999 | Haussinger | |
| 5,928,195 A | 7/1999 | Malamud et al. | |
| 5,961,999 A | 10/1999 | Bimczok et al. | |
| 6,008,221 A | 12/1999 | Smith et al. | |
| 6,056,958 A | 5/2000 | Mousa | |
| 6,228,875 B1 | 5/2001 | Tsai et al. | |
| 6,235,311 B1 | 5/2001 | Ullah et al. | |
| 6,287,765 B1 | 9/2001 | Cubicciotti | |
| 6,355,166 B1 | 3/2002 | Amarasinghe et al. | |
| 6,399,785 B1 | 6/2002 | Murphy et al. | |
| 6,476,006 B2 | 11/2002 | Flashner-Barak et al. | |
| 6,504,005 B1 | 1/2003 | Fridkin et al. | |
| 6,531,171 B2 | 3/2003 | Armand et al. | |
| 6,624,180 B2 | 9/2003 | South et al. | |
| 6,762,025 B2 | 7/2004 | Cubicciotti | |
| 6,855,734 B2 | 2/2005 | Messadek | |
| 6,881,420 B2 | 4/2005 | Flashner-Barak et al. | |
| 7,097,968 B2 | 8/2006 | Yuan et al. | |
| 2002/0012704 A1 | 1/2002 | Pace et al. | |
| 2002/0034757 A1 | 3/2002 | Cubicciotti | |
| 2002/0065320 A1 | 5/2002 | Messadek | |
| 2002/0183380 A1 | 12/2002 | Hunter | |
| 2002/0193307 A1 * | 12/2002 | Banting et al. ................. | 514/12 |
| 2003/0054978 A1 * | 3/2003 | Babish .............. | 514/2 |
| 2003/0124705 A1 | 7/2003 | Berry et al. | |
| 2003/0170223 A1 * | 9/2003 | Ahmad ........................ | 424/94.1 |
| 2003/0187074 A1 | 10/2003 | Hussain et al. | |
| 2003/0203385 A1 | 10/2003 | Venkataraman et al. | |
| 2003/0203878 A1 | 10/2003 | Flashner-Barak et al. | |
| 2004/0033223 A1 | 2/2004 | Messadek | |
| 2004/0043442 A1 * | 3/2004 | Jutila et al. ...................... | 435/18 |
| 2004/0067986 A1 * | 4/2004 | Sassover ........................ | 514/355 |
| 2004/0072750 A1 | 4/2004 | Phillips et al. | |
| 2004/0096499 A1 | 5/2004 | Vaya et al. | |
| 2005/0013866 A1 | 1/2005 | Maincent et al. | |
| 2005/0239719 A1 * | 10/2005 | Zeldis ............................. | 514/26 |
| 2006/0034918 A1 | 2/2006 | Messadek | |
| 2006/0128657 A1 | 6/2006 | Messadek | |
| 2006/0160896 A1 | 7/2006 | Messadek | |
| 2006/0233877 A1 | 10/2006 | Messadek et al. | |
| 2007/0134324 A1 | 6/2007 | Messadek | |

FOREIGN PATENT DOCUMENTS

| | | |
|---|---|---|
| BE | 1012546 | 12/2000 |
| BE | 1012712 | 2/2001 |
| BE | 2003/0248 | 4/2003 |
| DE | 19910682 | 9/2000 |
| EP | 0347864 | 12/1989 |
| EP | 0349902 | 1/1990 |
| EP | 0781554 | 7/1996 |
| FR | 2590 M | 6/1964 |
| FR | 70.47549 | 12/1970 |
| FR | 77 29075 | 9/1977 |
| HU | 210122 B | 9/1992 |

(Continued)

OTHER PUBLICATIONS

Zhang et al., Hypertension. 2004;44:935-943 (2004).*
Taddei et al. (Heart Fail Rev. Dec. 2001;6(4):277-285).*
Naproxen betainate Pharmaprojects, Applied Pharma Research, PJB Publications Ltd., Richmond, Surrey, UK, XP-002202249, pp. 1-2.
Naproxen monography from http://www.rxlist.com/, Clinical Pharmacology, pp. 1-2.
NIAID Home/Anti-HIV/OI Chemical Compound Search/Anti-HIV/OI Chemical Compound Results, http:chemdb.niaid.nih.gov/struct_search/all/url_search.asp?aids_no=008188, 1 page.

(Continued)

*Primary Examiner* — Daniel C Gamett

(57) ABSTRACT

The present invention relates to therapeutic compositions of betaines and L-arginine and physiologically acceptable salts thereof, and to pharmaceutical uses of betaines for up-regulating, enhancing, stimulating, controlling and/or increasing constitutive nitric oxide synthase expression a mammal, particularly in a human. Additionally, the betaines are believed to augment after administration both immunological and functional (activity) expression of Tissue Factor Pathway Inhibitor (TFPI) in a mammal, particularly a human.

22 Claims, No Drawings

FOREIGN PATENT DOCUMENTS

| | | |
|---|---|---|
| JP | 2000-143486 | 5/2000 |
| JP | 10321984 | 5/2000 |
| WO | 9515750 | 6/1995 |
| WO | 9706795 | 2/1997 |
| WO | 9738685 | 10/1997 |
| WO | WO 97/38686 | 10/1997 |
| WO | 9819690 | 5/1998 |
| WO | WO 98/56497 | 12/1998 |
| WO | WO 99/45913 | 9/1999 |
| WO | 0025764 | 5/2000 |
| WO | 0051596 | 9/2000 |
| WO | WO 01/56609 | 8/2001 |
| WO | WO 02/00213 | 1/2002 |
| WO | WO 02/47493 | 6/2002 |
| WO | WO 02/062322 | 8/2002 |
| WO | WO 02/066002 | 8/2002 |
| WO | WO 2004/032916 | 4/2004 |
| WO | WO 2004/049095 | 6/2004 |
| WO | WO 2004/091601 | 10/2004 |
| WO | WO 2005/004854 | 1/2005 |
| WO | WO 2005/011642 | 2/2005 |
| WO | WO 2005/011645 | 2/2005 |
| WO | WO 2005/065675 | 7/2005 |
| WO | WO 2006/007671 | 1/2006 |
| WO | WO 2006/050581 | 5/2006 |

OTHER PUBLICATIONS

Bonaa et al., Homocysteine lowering and cardiovascular events after acute myocardial infarction,: N. Eng. J. Med., Apr. 13, 2006; 354(15):1578-88. Epub Mar. 12, 2006.
Lonn et al., "Homocysteine lowering folic acid and B vitamins in vascular disease," N. Eng. J. Med., Apr. 13, 2006,354(15):1567-77. Epub Mar. 12, 2006.
Tafreshi, Medical Management of Peripheral Arterial Disease, Pharmacy Times, Bristol-Myers Squibb Company grant, 11 pages.
Carman and Fernandez, "A Primary Care Approach to the Patient with Claudication," American Family Physician, vol. 61, No. 4, Feb. 15, 2000, http://www.aafp.org/afp/20000215/1027.html, 8 pages.
Beaufour and Beaufour, "Nouvelles associations antinévralgiques à tolérance améliorée," Brevet Spécial De Médicament, P.V. No. 927.734, No. 2.590, 1964, pp. 1-5.
Feb. 23, 1996 Chinese document (pp. 91-93) with English translation titled "Homocysteine and Vascular Disease," 5 pages.
Da Silva and Sobel, Abstract from Entrez-PubMed web page entitled "Anicoagulants: to bleed or not to bleed, that is the question," Semin Vasc. Surg. Dec. 2002;15(4):256-67, 1 page.
JACC Abstracts, Myocardial Ischemia and Infarction, Feb. 2000, 1196-107, pp. 408-409.
Lasch H.G., Abstract from Entrez-PubMed web page entitled "Principles of Drug Prevention of Thrombosis," Langenbecks Arch Chir., 1986;369:451-7, 1 page.
Marcel et al., Abstract from Entrez-PubMed web page entitled "From Virchow to red cells (the unended quest).", Ric Clin Lab., 1983;13 Suppl 3:71-81, 1 page.
I. Züllei et al., Betaine-Palmitate Reduces Acetylsalicyclic Acid-induced Gastric Damage in Rats, Scand J. Gastroenterol 2001 (8), pp. 811-816.
Antithrombotic effect of Betaine, Bio Ethic, Jan. 2003, pp. 1-30.
Office Action in U.S. Appl. No. 09/945,391 dated Nov. 5, 2002, 5 pages.
Office Action in U.S. Appl. No. 09/945,391 dated Jun. 4, 2003, 14 pages.
Office Action in U.S. Appl. No. 10/635,048 dated Dec. 6, 2005, 8 pages.
Office Action in U.S. Appl. No. 10/635,048 dated Dec. 21, 2006, 16 pages.
Office Action in U.S. Appl. No. 10/635,048 dated Sep. 20, 2007, 25 pages.
Bidulescu et al., Usual choline and betaine dietary intake and incident coronary heart disease: the Atherosclerosis Risk in Communities (ARIC) Study,BMC Cardiovasc Disord. 2007, 7:20.
Hallas et al., "Use of single and combined antithrombotic therapy and risk of serious upper gastrointestinal bleeding: population based case-control study," BMJ 2006:333:726, Oct. 7, 2006.
Cassar, "Intermittent Claudication," BMJ, vol. 333, Nov. 11, 2006, pp. 1002-1005.
Apgar, "Efficacy of Cilostazol for Intermittent Claudication," American Family Physician, Feb. 15, 2000, 2 pages.
Girolami et al., "Treatment of Intermittent Claudication with Physical Training, Smoking Cessation, Pentoxifylline, or Nafronly," Arch Intern med, 1999;159:337-345.
Giaid et al, "Expression of Endothelin-1 in the Lungs of Patients with Pulmonary Hypertension," NEJM, vol. 328:1732-1739, No. 24, Jun. 17, 1993, 2 pages.
Giaid et al., "Reduced Expression of Endothelial Nitric Oxide Synthase in the Lungs of Patients with Pulmonary Hypertension," NEJM, vol. 333:214-221, No. 4, Jul. 27, 1995, 2 pages.
Office Action in U.S. Appl. No. 11/251,737 dated Apr. 17, 2008, 7 pages.
Office Action in U.S. Appl. No. 11/333,514 dated Sep. 20, 2007, 12 pages.
Office Action in U.S. Appl. No. 11/333,514 dated Nov. 15, 2007, 11 pages.
McGregor et al, "A Controlled Trial of the Effect of Folate Supplements on Homocysteine, Lipids and Hemorheology in End-State Renal Disease," Nephron, vol. 85, No. 3, 2000, 215-220.
Gurfinkel et al., "Fast platelet suppression by lysine acetylsalicylate in chronic stable coronary patients. Potential clinical impact over regular aspirin for coronary syndromes," Clin. Cardiol., Sep. 2000;23(9):697-700.
Klasing et al., "Dietary Betaine Increases Intraepithelial Lymphocytes in the Duodenum of Coccidia-Infected Chicks and Increases Functional Properties of Phagocytes," 2002, The American Society for Nutritional Sciences, J. Nutr, 132:2274-2282, 2002.
Schmidt et al., "Total nitric oxide production is low in patients with chronic renal disease," Kidney International, 2000, 58, 1261-1266.
Letter Regarding Dietary Supplement Health Claim for Folic Acid, Vitamin B6, and Vitamin B12 and Vascular Disease, to Jonathan W. Emord of Emord & Associates, PC, from Christine J. Lewis of the FDA, Nov. 28, 2000.
Malinow, "Plasma homocyst(e)ine and arterial occlusive diseases: a mini-review " Clin. Chem, Jan. 1995; 41(1):173-6.
al Awami et al., "Homocysteine levels in patients with Raynaud's phenomenon," Vasa. May 2002; 31(2): 87-90.
Stammler et al., "The prevalence of hyperhomocysteinemia in thromboangitis obliterans. Does homocysteine play a role pathogenetically?" Dtsch Med Wochenschr, Nov. 15, 1996;121(46):1417-23.
English Translation of French Patent 2,590M issued on Jun. 15, 1964, 11 pages.
McCarty, "Co-administration of equimolar doses of betaine may alleviate the hepatotoxic risk associated with niacin therapy," Med-Hypothesis, Sep. 2000; 55(3): 189-94.
Letter regarding Petition for Health Claim: Folic Acid, Vitamin B6, and Vitamin B12 Dietary Supplements and Vascular Disease, to Jonathan W. Emord of Emord & Associatees from Christine J. Lewis of the FDA, Feb. 9, 2001.
Birnie et al., "Antimicrobial Evaluation of N-Alkyl Betaines and N-Alkly-N,N-Dimethylamine Oxides with Variations in Chain Length," Antimicrobial Agents and Chemotherapy, Sep. 2000, p. 2514-2517.
Palatka Karoly at al., "Changes in the expression and distribution of the inducible and endothelial nitric oxide synthase in mucosal biopsy specimens of inflammatory bowel disease," Scandinavian Journal of Gastroenerology, 2005, vol. 40, No. 6, pp. 670-680.
van Hoek, "Non-alcoholic fatty liver disease: a brief review," Scandinavian Journal of Gastroenerology Supplement, 2004;(241):56-9.
Mendes et al., "Recent advances in the treatment of non-alcoholic fatty liver disease," Expert Opin. Investig. Drugs, Jan. 2005;14(1):29-35.
Hiatt et al, Long-term safety of cilostazol in patients with peripheral artery disease: The CASTLE study (Cilostazol: A Study in Long-term Effects), Journal of Vascular Surgery, vol. 47, No. 2, pp. 330-336, Feb. 2008.
Korzh, "Relationship Between Endothelial Nitric Oxide Synthesis and Low-Grade Chronic Inflammation," European Atherosclerosis Society, 73rd EAS Congress, Salzburg, Austria, Jul. 7-10, 2002.

Didier et al., "Distal cutaneous necrosis, an unusual etiology: hyperhomocysteinemia," Ann Dermatol Venereol, Nov. 1999;126(11):822-5; PMID: 10612875.

Gurfinkel et al., "Fast Platelet Suppression by Lycine Acetylsalicylate in Chronic Stable Coronary Patients. Potential Clinical Impact Over Regular Aspirin for Coronary Syndromes," Abstracts—Myocardiol Ischemia and Infarction, JACC, Feb. 2000, 408A-409A.

Bonaa at al., Homocysteine lowering and cardiovascular events after acute myocardial infarction,: N. Eng. J. Med., Apr. 13, 2006; 354(15):1578-88. Epub Mar. 12, 2006.

Lonn et al., "Homocysteine lowering folic acid and B vitamins in vascular disease," N. Eng. J. Med., Apr. 13, 2006;354(15):1567-77. Epub Mar. 12, 2006.

Approval of Cilostazol, Jan. 6, 2006, Center for Drug Evaluation and Research, www.fda.gov/cder/news/cilostazol/appproval.htm.

Tafreshi, Medical Management of Peripheral Arterial Disease, Pharmacy Times, Bristol-Myers Squibb Company grant, 11 pages, Nov. 2003.

Diagnosis and Management of Peripheral Arterial Disease: A National Clinical Guideline, Scottish Intercollegiate Guidelines Network, Oct. 2006, www.sign.ac.uk.

Hiatt, "Medical Treatment of Peripheral Arterial Disease and Claudication," N Engl J Med, vol. 344, No. 21, May 24, 2001, pp. 1608-1621.

Hiatt, "The US experience with cilostazol in treating intermittent claudication," Atherosclerosis Supplements 6 (2006) 21-31.

Office Action dated Dec. 8, 2011 in related U.S. Appl. No. 12/558,973, filed Sep. 14, 2009.

Office Action dated Apr. 20, 2012 in related U.S. Appl. No. 12/868,592, filed Aug. 25, 2010.

Office Action dated Aug. 6, 2008 in related U.S. Appl. No. 10/635,048, filed Aug. 4, 2003.

Office Action dated Jul. 27, 2010 in related U.S. Appl. No. 12/558,973, filed Sep. 14, 2009.

Office Action dated Mar. 1, 2011 in related U.S. Appl. No. 12/558,973, filed Sep. 14, 2009.

Lacy et al., Drug Information Handbook, 7th Edition 1999-2000, p. 140.

Lacy et al., Drug Information Handbook, 7th Edition 1999-2000, pp. 285-286.

Office Action dated Jul. 13, 2009 in related U.S. Appl. No. 10/536,584, filed Apr. 7, 2006.

Office Action dated Feb. 25, 2010 in related U.S. Appl. No. 10/536,584, filed Apr. 7, 2006.

Lacy et al., Drug Information Handbook, 1999-2000, Lexi-Comp, pp. 90-93.

Office Action dated Apr. 17, 2008 in related U.S. Appl. No. 11/251,737, filed Oct. 17, 2005.

Office Action dated Dec. 14, 2011 in related U.S. Appl. No. 12/704,294, filed Feb. 11, 2010.

Office Action dated Oct. 29, 2008 in related U.S. Appl. No. 11/251,737, filed Oct. 17, 2005.

Office Action dated Sep. 10, 2009 in related U.S. Appl. No. 11/251,737, filed Oct. 17, 2005.

Office Action dated Sep. 8, 2008 in related U.S. Appl. No. 11/333,514, filed Jan. 17, 2006.

Hiatt, "New Treatment Options in Intermittent Claudication: The US Experience," International Journal of Clinical Practice (2001) 119:20-27.

Office Action dated Mar. 20, 2009 in related U.S. Appl. No. 11/333,514, filed Jan. 17, 2006.

Office Action dated Sep. 17, 2009 in related U.S. Appl. No. 11/333,514, filed Jan. 17, 2006.

Office Action dated Jan. 28, 2009 in related U.S. Appl. No. 11/348,142, filed Feb. 6, 2006.

Office Action dated Jun. 9, 2011 in related U.S. Appl. No. 12/510,034, filed Jul. 27, 2009.

Office Action dated Mar. 26, 2012 in related U.S. Appl. No. 12/704,294, filed Feb. 11, 2010.

Office Action dated Sep. 19, 2011 in related U.S. Appl. No. 12/726,109, filed Mar. 17, 2010.

Office Action dated Nov. 10, 2011 in related U.S. Appl. No. 12/726,109, filed Mar. 17, 2010.

Malinow, "Plasma Homocyst(e)ine and Arterial Occlusive Diseases: a Mini-Review," Clin. Chem., 40/1, 173-176, 1994.

Andersson et al., "Long-term outcome in treated combined methylmalonic acidemia and homocystinemia," Genetics in Medicine, May/Jun. 1999, vol. 1, No. 4, pp. 146-150.

Office Action dated Dec. 9, 2009 in related U.S. Appl. No. 11/838,788, filed Aug. 14, 2007.

Office Action dated Apr. 10, 2009 in related U.S. Appl. No. 11/927,172, filed Oct. 29, 2007.

Office Action dated Jul. 9, 2009 in related U.S. Appl. No. 11/927,172, filed Oct. 29, 2007.

Varga et al., "Homocysteine and MTHFR Mutations: Relation to Thrombosis and Coronary Artery Disease," American Heart Association, 2005, 111:e289-e293.

Albert et al., "Effect of Folic Acid and B Vitamins on Risk of Cardiovascular Events and Total Mortality Among Women at High Risk for Cardiovascular Disease: A Randomized Trial," JAMA. 2008, 299(17):2027-2036.

Office Action dated Apr. 16, 2012 in related U.S. Appl. No. 12/726,109, filed Mar. 17, 2010.

Office Action dated Nov. 10, 2011 in related U.S. Appl. No. 12/510,034, filed Jul. 27, 2009.

Office Action dated Sep. 2, 2010 in related U.S. Appl. No. 11/625,448, filed Jan. 22, 2007.

Office Action dated Feb. 2, 2011 in related U.S. Appl. No. 11/625,448, filed Jan. 22, 2007.

Remington, "The Science and Practice of Pharmacy," 19th Edition, 1995, Chapter 91, p. 1612, Mack Publishing Company.

Office Action dated Sep. 6, 2011 in related U.S. Appl. No. 11/625,448, filed Jan. 22, 2007.

Office Action dated Apr. 24, 2012 in related U.S. Appl. No. 12/783,377, filed May 19, 2010.

Savi et al., Abstract from Entrez-PubMed web page entitled "SR 121787, a new orally active fibrinogen receptor antagonist," Thromb Haemost, Sep. 1998;80(3):469-76., 1 page.

Banno et al., Abstract from Entrez-PubMed web page entitled "Antiaggregatory, antithrombotic effects of MS-180, a novel platelet glycoprotein IIb/IIIa receptor antagonist," Eur J Pharmacol., Feb. 19, 1999;367(2-3):275-82., 1 page.

Ramjit et al., Abstract from Entrez-PubMed web page entitled "Antithrombotic effects of MK-0852, a platelet fibrinogent receptor antagonist, in canine models of thrombosis," J Pharmacol Exp Ther., Sep. 1993,266(3):1501-11, 2 pages.

Hoffmann et al., Abstract from Entrez-PubMed web page entitled "Prevention of thrombosis and enhancement of thrombolysis in rabbits by SR 121787, a glycoprotein II/III antagnoist," J Pharmacol Exp Ther., Aug. 1998;286(2):670-5., 1 page.

Packham, Abstract from Entrez-PubMed web page entitled "Role of platelets in thrombosis and hemostasis." Can J Physiol Pharmacol., Mar. 1994;72(3):278-84., 1 page.

Lynch et al., Abstract from Entrez-PubMed web page entitled "Nonpeptide glycoprotein IIb/IIIa inhibitors. 5. Antithrombotic effects of MK-0383," J Pharmacol Exp Ther., Jan. 1995;272(1):20-32., 2 pages.

Katada et al., Abstract from Entrez-PubMed web page entitled "The in vitro and in vivo pharmacological profiles of a platelet glycoprotein IIb/IIIa antagonist, NSL-9403," Thromb Res., Oct. 1, 1997;88(1):27-70., 1 page.

Ogawa et al., Abstract from Entrez-PubMed web page entitled "Antiplatelet and antithrombotic effects of orbofiban, a new orally active GPIIb/IIIa antagonist, in guinea pigs," Thromb Res., Mar. 1, 2000;97(5):307-15., 1 page.

Zapadniuk, Abstract from Entrez-PubMed web page entitled "Cholagogic effect of trimethylglycine in normal animals of different ages and in experimental atherosclerosis," Biull Eksp Biol Med., Jul. 1987:104(7)30-2., 2 pages.

Panteleimonova, Abstract from Entrez-PubMed web page entitled "Effect of trimethylglicine on lipid metabolism in experimental atherosclerosis in rabbits," Farmakol Toksikol, Jul.-Aug. 1983;46(4):83-5., 1 page.

Fazio et al., "Treatment of Human Atherosclerosis with Betaine," Minerva Med, Apr. 25, 1961, pp. 1511-1516, XP-000853747.

P.H. List et al., "Hagers Handbuch Der Pharmazeutischen Praxis," 1972, Pringer Verlag, Berlin Heidelberg, New York, p. 431, XP-002123167.

Wilcken et al., "The natural history of vascular disease in homocystinuria and the effects of treatment," J. Inher. Metab. Dis. 20(1997) 295-230.

Betaine for Homocystinuria, The Medical Letter, vol. 39, Issue 993, Jan. 31, 1997, p. 12, XP-000853853.

Reynolds, Betaine Hydrochloride, Matindale, The Extra Pharmacopoeia, 1996, Royal Pharmaceutical Society, London, p. 1679, XP-002123168.

1225. Betaine, The Merck Index, 1996 Merck and Co., Whithouse Stations, NJ, p. 198, XP-002123169.

Mar et al., Abstract from Entrez-PubMed web page entitled "Betaine in wine: answer to the French paradox?" Med Hypotheses, Nov. 1999;53(5):383-5., 2 pages.

Salamone et al, "Changes in blood coagulation in experimental subacute poisoning with p-dichlorobenzene. The influence of some lipotropic factors," Journal, Answer 13 of 13, Copyright 2003, ACS, 1 page.

Vinson et al., "New Drug Approvals of 1996-Part 3," Drug Topics, Mar. 17, 1997, University of Mississippi School of Pharmacy, pp. 72-81.

Naproxen betainate Pharmaprojects, Applied Pharma Research, PJB Publications Ltd., Richmond, Surrey, UK, XP-002202249, pp. 1-2, Sep. 1995.

Matthews et al., An indirect response model of homocysteine suppression by betaine: optimising the dosage regimen of betaine in homocystinuria,: 2002 Blackwell Scient Ltd Br J Clin Pharmacol, 54, 140-146.

Schwahn et al, "Pharmacokinetics of oral betaine in healthy subjects and patients with homocystinuria," 2003 Blackwell Scient Ltd Br J Clin Pharmacol, 55, 6-13.

Naproxen monography from http://www.rxlist.com/, Clinical Pharmacology, pp. 1-2, 2002.

Bandfield et al., "Naproxen, Naproxen Sodium, and Naproxen Betainate Sodium Monohydrate Salts," Pharmaceutics 1, Apr. 14, 2001, pp. 1-5.

van Hecken et al., Abstract from Entrez-PubMed web page entitled "Effect of clopidogrel on naproxen-induced gastrointestinal blood loss in healthy volunteers," Drug Metabol Drug Interact, 1998;14(3):193-205., 1 page.

EC-Naprosyn, Naprosyn, Anaprox, Naprosyn, RX Only, Roche Pharmaceuticals, Copyright 1999-2004 by Roche Laboratories Inc., pp. 1-20.

Environmental and Health Assessment of Substances in Household Detergents and Cosmetic Detergent Products, Environment Project, 615, 2001, 6.1 Betaines, http:www2.mst.dk/common/Udgivramme/Frame.asp?pg=http://www2.mst.dk/udgiv/Publications/2001/87-7944-596-9/html/helepubl_eng.htm, 1 page.

NIAID Home/Anti-HIV/OI Chemical Compound Search/Anti-HIV/OI Chemical Compound Results, http:chemdb.niaid.nih.gov/struct_search/all/url_search.asp?aids_no=008188, 1 page, 2004.

Wyrick P.B. et al., The Microbicidal Agent C31G Inhibits Chlamydia Trachomatis Infectivity in vitro., *Antimicrob Agents Chemother*, Jun. 1997, 41(6): 1335-44, PMID: 9174195, 1 page.

Thompson, K.A. et al., Assessment of the Anti-Microbial Agent C31G as a Spermicide: Comparison with Nonoxynol-9, *Contraception*, May 1996, 53(5): 313-8, PMID: 8724622, 1 page.

Rogers J.S., Abstract from Entrez-PubMed web page entitled "Hypercoagulable states," W V Med J., Feb. 1993;89(2):61-3, 1 page.

Nielsen H.K., Abstract from Entrez-PubMed web page entitled "Pathophysiology of venous thromboembolism," Semin Thromb Hemost, 1991;17 Suppl 3:250-3, 1 page.

Silver et al., Abstract from Entrez-PubMed web page entitled "The caput medusae of hypercoagulability," J. Vasc. Surg., Feb. 2000;31(2):396-405, 1 page.

Swan M.A., "Improved Preservation of the Ram Spermatozoan Plasma Membrane using Betaine in the Primary Fixative," J. Microsc., Sep. 1997, 187(pt 3): 167-9, PMID: 9351233, 1 page.

Thomas, K.C. at al., Effects of Particulate Materials and Osmoprotectants on Very-High-Gravity Ethanolic Fermentaiont by *Saccharomyces cerevislae*, Appl Environ Microbiol, May 1994, 60(5): 1519-24, PMID: 801734, 1 page.

Chambers, S. et al., The Osmoprotective Properties of Urine for Bacteria: The Protective Effect of Betaine and Human Urine Against Low pH and High Concentrations of Electrolytes, Sugars, and Urea, *J. Infect Dis.*, Dec. 1985, 152(6): 1308-16, PMID: 3905988, 1 page.

Smith, L.T., Role of Osmolytes in Adaptation of Osmotically Stressed and Chill-Stressed Listeria Monocytogenes Grown in Liquid Media and on Processed Meat Surfaces, *Appl Environ Microbiol*, Sep. 1996, 62(9): 3088-93, PMID: 8795194, 1 page.

Peddie B.A. et al., Is the Ability of Urinary Tracy Pathogens to Accumulate Glycine Betaine a Factor in the Virulence of Pathogenic Strains?, *J. Lab. Clin. Med.*, Oct. 1996, 128(4): 417-22, PMID: 8833891, 1 page.

Koskinen, E. et al., A Preliminary Study on the Use of Betaine as a Cryoprotective Agent in Deep Freezing of Stallion Semen, *Zentralbl Veterinarmed A.*, Feb. 1989, 36(2): 110-4, PMID: 2501949, 1 page.

Swan M.A., Improved Preservation of Ultrastuctural Morphology in Human Spermatozoa Using Betaine in the Primary Fixative, Int. J. Androl., Feb. 20, 1997(1):45-54, PMID: 9202990, 1 page.

* cited by examiner

MODULATION OF NITRIC OXIDE SYNTHASES BY BETAINES

This application is a CIP application of (1) PCT/BE2005/00161 filed on 9 Nov. 2005, published under number WO2006/050585 on 18 May 2005, claiming the priority of PCT/BE2004/00163 filed on 10 Nov. 2004 and PCT/BE2005/00006 filed on 19 Jan. 2005; and (2) PCT/BE2006/000082 filed 20 Jul. 2006 and published under number WO2008/009071 on 24 Jan. 2008. Applicant claims the priority benefit of each of PCT/BE2005/00161 filed 9 Nov. 2005, PCT/BE2004/00163 filed 10 Nov. 2004, and PCT/BE2005/00006 filed 19 Jan. 2005, the disclosures of which are incorporated herein by reference. Applicant also claims the priority benefit of PCT/BE2006/000082 filed 20 Jul. 2006.

BACKGROUND OF THE INVENTION

The present invention relates to the pharmaceutical uses of betaines for up-regulating, enhancing, stimulating, controlling and/or increasing constitutive nitric oxide synthase expression and constitutive nitric oxide production or levels in a mammal, particularly in a human. Additionally, the betaines are claimed to augment after administration both immunological and functional (activity) expression of Tissue Factor Pathway Inhibitor (TFPI) in a mammal, particularly in a human.

STATE OF THE ART

The pharmacological uses of betaines for treatment of specific conditions have been described by the inventor, notably its anticoagulant uses in different specifications. But in any of these descriptions, no mention was made concerning the ability of betaine to enhance constitutive nitric oxide synthase expression and nitric oxide production in a living body. Surprisingly it was found that betaines possess excellent abilities to enhance and/or to control constitutive nitric oxide production in the body after administration, advantageously oral administration, and especially ingestion.

U.S. Pat. No. 5,880,098 by Haussinger Dieter, describes the use of osmolytes, among them betaine, for treating complications which involve an increase in the activity of inducible nitric oxide synthase (iNOS). This is recited in claim 4 of this patent as in the description of the invention of this reference where mention is made asserting, "[t]hese complications typically can involve phenomena as cell death exemplified by programmed cell death (apoptosis) and necrosis, as well as an increase in the activity of inducible nitric oxide synthase (iNOS)".

This down-regulating activity of osmolytes is furthermore showed and claimed in the examples of this reference, to wit: "FIG. 8 shows that osmolytes are effective in down-regulating inducible nitric oxide synthase (iNOS). As INOS is a mediator of complications following ischemia, hypoxia and oxidative stress, these results support the utility of osmolytes in the treatment of reducing complications resulting from said stress situations". Thus, in this reference no mention is made to constitutive nitric oxide synthase, nor to the ability of betaine in up-regulating, i.e. enhancing or increasing constitutive nitric oxide synthase expression, nor is mention made to the ability of betaine to increase and/or control nitric oxide production in a mammal, particularly in a humans.

U.S. Pat. Nos. 6,008,221 & 6,127,370 by Smith Anthony David & Jobst Kim Anthony, relate to methods for inhibiting or preventing microvascular events leading to ischemia and/or neuro-degeneration, such as in occlusive vascular disease, or in Alzheimer's disease, wherein the patient has at least moderately elevated blood levels of homocysteine and at least moderately reduced blood levels of folate and vitamin B.sub.12. The use of betaine to lower homocysteine levels combined to nitric oxide donors is described, but in these patents no mention is made to constitutive nitric oxide synthase, nor to the ability of betaine in up-regulating, i.e. enhancing or increasing constitutive nitric oxide synthase expression, nor to betaine ability to increase nitric oxide production in a mammal, particularly in a human.

SUMMARY OF THE INVENTION

Nitric oxide (NO) is a key molecule that, either directly or through intracellular signalling, stimulates host defences in the immune system, maintains blood pressure in the cardiovascular system and modulates neural transmission in the brain. NO is an activator of soluble guanylyl cyclase, which converts guanosine triphosphate (GTP) to cyclic guanosine monophosphate (cGMP), leading to vasodilatation and inhibition of leukocyte and platelet activation. As the biologically active component of endothelium-derived relaxing factor, NO has critical roles in the maintenance of vascular homeostasis. NO acts as a neurotransmitter in the central and peripheral nervous systems and, therefore, is critical in the pathogenesis of stroke and other neurodegenerative disorders. As a signal transducer in mammalian systems, NO covalently interacts with target molecules based on redox potential. Finally, as a highly reactive chemical, NO directly regulates the activity of many proteins, such as kinases and proteases.

Nitric oxide synthase (NOS) catalyses the oxidation of the terminal guanidino nitrogen of the amino acid L-arginine to produce NO and L-citrulline. Three distinct forms of NOS have been described: neuronal NOS, endothelial NOS and inducible NOS. Neuronal and endothelial NOS are regulated by physiological changes in intracellular calcium concentrations, whereas inducible NOS appears to be regulated in a cell-specific manner.

Pharmacological compounds that release nitric oxide (NO) have been useful tools for evaluating the broad role of NO in physiology and therapeutics. NO deficiency has been implicated in the genesis and evolution of several disease states. Both medical needs and commercial opportunities have fostered attempts to modulate NO in the human body for therapeutic gain. Strategies for NO modulation encompass antiinflammatory, sexual dysfunction, and cardiovascular indications. Apart from newly developed drugs, several commonly used cardiovascular drugs exert their beneficial action, at least in part, by modulating the NO pathway. This present specification describes the use of betaines of general formula $(CH_3)_3N^+-(CH_2)n\text{-}COO^-$) n being an integer from 1 to 5, as the fundamental pharmacological properties and mechanisms of action of betaines NO-releasing drugs. Some of these betaines compounds may enter in the clinical arena providing important therapeutic benefits in human diseases.

Nitric oxide (NO), a small molecule is a key messenger in mammalian physiology. NO is produced in humans by three related enzymes which comprise the nitric oxide synthase (NOS) family.

Endothelial NOS (ENOS) produces NO which controls vascular tone (hence blood pressure), dilates the airways, and controls numerous processes dependent on local dilation of blood vessels (such as gas exchange in lungs, penile erection, and renal function). Brain or neuronal NOS (BNOS or NNOS) produces NO which functions as a neurotransmitter. It controls peristalsis in the gut, and is implicated in neural potentiation and brain development. NNOS, platelet NOS and ENOS are constitutive enzymes controlled by intracellular calcium and the regulatory protein calmodulin (CAM). When the level of calcium in the cell rises, NNOS, platelet NOS and ENOS bind calmodulin and are turned on to start NO production.

A third, inducible NOS, immune NOS or macrophage NOS (INOS or MNOS), is synthesized by the immune system in response to an immune challenge. Upon induced expression, this enzyme is always active; it has a calmodulin binding site, but binds calmodulin tightly even at very low calcium levels. INOS produces orders of magnitude more NO than other NO synthases. This NO level is cytotoxic to tumour cells, bacteria, and other pathogenic organisms.

While INOS thus appears to be an important component of immune response, its activity is highly toxic as well. Excess production of NO by INOS can be responsible for toxic shock syndrome, septic shock, and killing of islet cells in diabetes. Excess NO production by INOS has also been implicated in a wide range of other autoimmune conditions, including arthritis and other inflammatory conditions.

Thus, it is of critical importance to learn to control NO synthesis by one NOS, without interfering with the activity of other NO synthases such as Inducible NO synthases. The goal of the present invention is to provide a molecule, namely betaine, which is capable to enhance and/or upregulate NO synthesis in the body through calcium dependent NO synthases, namely constitutive NO synthases such as Endothelial NOS (ENOS), Platelet NOS (PNOS), Brain or neuronal NOS (BNOS or NNOS) while having no enhancing effects on inducible NOS (INOS).

According to an aspect of the invention, a method is provided for increasing endothelial cell Nitric Oxide Synthase activity in a subject to treat a condition favourably affected by an increase in endothelial cell Nitric Oxide Synthase activity in a tissue. Such conditions are exemplified above. The method involves administering to a subject in need of such treatment a betaine in an amount effective to increase endothelial cell Nitric Oxide Synthase activity in the tissue of the subject.

According to another aspect of the invention, a method is provided for reducing brain injury resulting from stroke. The method involves administering to a subject having an abnormally high risk of an ischemic stroke an effective amount of a betaine to increase endothelial cell Nitric Oxide Synthase activity in the brain of the subject According to another aspect of the invention, a method is provided for treating pulmonary hypertension. The method involves administering to a subject in need a betaine in an amount effective to increase pulmonary endothelial cell Nitric Oxide Synthase activity in the subject. Particularly important embodiments are as described above in connection with the methods for treating brain injury. Another important embodiment is administering the agent prophylactically to a subject who has an abnormally elevated risk of developing pulmonary hypertension, including subjects that are chronically exposed to hypoxic conditions.

According to another aspect of the invention, a method for treating heart failure and chronic heart failure is provided. The method involves administering to a subject in need of such treatment a betaine in an amount effective to increase vascular endothelial cell and/or platelet Nitric Oxide Synthase activity in the subject. Such enhanced NO production contributing to lower both arterial and venous tones.

According to the invention, clinical Implications of betaines therapies are numerous: The majority of blood volume lies within the venous capacitance bed; hence, small changes in venous tone may translocate relatively large volumes of blood to or from the central compartment. Such shifts in central blood volume will alter right ventricular and consequently left ventricular end-diastolic volume and will as a result, via the Frank-Starling mechanism, affect stroke work. Thus the venous endothelium, via its effect on venous tone, can significantly influence stroke work and hence cardiac output. This has particular relevance in chronic heart failure (CHF), in which increased central blood volume, mediated in part by increased venous tone, appears to have a deleterious effect on cardiac performance. If endothelial dysfunction contributes to increased venous tone in CHF, betaines targeted at improving endothelial function will provide a novel strategy for veno-dilator therapy.

In the heart, nitric oxide synthases (NOS) modulate cardiac contraction in an isoform-specific manner, which is critically dependent on their cellular and sub-cellular localization. Defective NO production by NOS3 (endothelial NOS [eNOS]) in the failing heart may precipitate cardiac failure, which could be reversed by over-expression of NOS3 in the myocardium, such over-expression according to the present invention being reached by betaine pharmacological interventions.

As discussed above, important embodiments include prophylactic and acute administration of the agent(s). Preferred compounds and co-administration schemes are as described above.

According to yet another aspect of the invention, a method for treating progressive renal disease is provided. The method involves administering to a subject in need of such treatment a betaine in an amount effective to increase renal endothelial cell Nitric Oxide Synthase activity in the kidney of the subject. Important embodiments and preferred compounds and schemes of co-administration are as described above in connection with heart failure.

According to another aspect of the invention, a method for increasing blood flow in a tissue of a subject is provided. The method involves administering to a subject in need of such treatment a betaine and a first agent that disrupts actins cytoskeletal organization in an amount effective to increase endothelial cell Nitric Oxide Synthase activity in the tissue of the subject. In other embodiments the first agent is selected from the group consisting of a myosin light chain phosphatase, a protein kinase N inhibitor, a phospatidylinositol 4-phosphate 5-kinase inhibitor, and cytochalasin D. Other important embodiments include co-administering a second agent to the subject with a condition treatable by the second agent in an amount effective to treat the condition, whereby the delivery of the second agent to a tissue of the subject is enhanced as a result of the increased blood flow. In certain embodiments where a second agent is administered, the conditions treatable by the second agent involve the brain tissue.

The invention also involves the use of agents that disrupt actin cytoskeletal organization in combination with betaines in the manufacture of medicaments for treating the above-noted conditions. Important conditions, compounds, etc. are as described above. The invention further involves pharmaceutical preparations that are cocktails of agents that disrupt actin cytoskeletal organization according to the invention [non-rho GTPase function inhibitor(s)]. In certain embodiments, however, the cocktails can include a rho GTPase function inhibitor(s) that disrupts actin cytoskeletal organization together with the non-rho GTPase function inhibitor agent of the invention. The invention also involves pharmaceutical preparations that are cocktails of betaines and agents that disrupt actin cytoskeletal organization together optionally with agents other than agents that disrupt actin cytoskeletal organization that also increase NOS activity in a cell.

The invention also involves methods for increasing NOS activity in a cell by contacting the cell with an effective amount of a betaine, alone, or together with any of the agents co-administered as described above, or as a cocktail as described above.

The invention also involves the uses of betaines as agonists to endogenous nitric oxide production in a tissue, cells, blood, organs and living mammal bodies. "Agonist" refers to an agent who stimulates the bio-transformation of a NO precursor, such as L-arginine or L-lysine to endogenous NO either through enzymatic activation, regulation or increasing gene expression (i.e., increased protein levels of c-NOS). Of course, either or both of these mechanisms may be acting simultaneously.

The invention relates also to the use of betaine for the preparation of nutriment or nutritional composition having specific health benefits. Betaine acts in such composition as health promoter or promoting agent or as health co-promoter or health co-promoting agent. The nutritional composition comprises advantageously betaine and a compound selected from the group consisting of soy, soy derivatives and/or soy isoflavones. Such a composition comprises advantageously more than 0.5% by weight betaine (especially glycine betaine), preferably more than 1% by weight betaine (especially glycine betaine), most preferably between 2% and 20% by weight betaine (glycine betaine), such as 3% by weight, 5% by weight, 7% by weight, 10% by weight, 12% by weight, 15% by weight, 18% by weight. Higher betaine content is possible in specific case, such as 25% by weight, 35% by weight, etc.

The invention further relates to a nutritional composition for administration to humans for woundcare or reducing or preventing effects due to pressure ulcers. As stated by Numico: "Woundcare is a key issue for carers and patients alike. Pressure ulcers (decubitus) are typically found on areas of the body where bones protrude. They form when these areas are subjected to unusual pressure, friction or shear forces for long periods of time (e.g. patients who are lying or seated in one and the same position over a continued period of time) or high pressure for a relatively short period of time (e.g. during surgery). The nutritional composition comprises advantageously further at least one compound selected from the group consisting of arginine (especially L-arginine), zinc, vitamins A, B, C and E, and other antioxidants such as selenium and carotenoids, and mixtures thereof. Such a composition comprises advantageously more than 0.5% by weight betaine (especially glycine betaine), preferably more than 1% by weight betaine (especially glycine betaine), most preferably between 2% and 20% by weight betaine (glycine betaine), such as 3% by weight, 5% by weight, 7% by weight, 10% by weight, 12% by weight, 15% by weight, 18% by weight. Higher betaine content is possible in specific case, such as 25% by weight, 35% by weight, etc.

The invention further relates to a nutritional composition for administration to humans for treating Dysphagia. According to Numico, Dysphagia is a condition in which the action of swallowing is either painful or difficult to perform. It can affect key phases in swallowing—the oropharyngeal and oesophageal phases and is usually accompanied by reductions in food and fluid intake and rapid weight loss. Oropharyngeal dysphagia can occur in patients with neuromuscular disorders, such as Parkinson's disease and motor neurone disease, stroke and head injury patients or in those with physical obstruction of the pharynx (e.g. by cancer).

The nutritional composition advantageously comprises betaine and at least one compound selected from the group consisting of protein, minerals, antioxidants and mixtures thereof. Such a composition comprises advantageously more than 0.5% by weight betaine (especially glycine betaine), preferably more than 1% by weight betaine (especially glycine betaine), most preferably between 2% and 20% by weight betaine (glycine betaine), such as 3% by weight, 5% by weight, 7% by weight, 10% by weight, 12% by weight, 15% by weight, 18% by weight. Higher betaine content is possible in specific case, such as 25% by weight, 35% by weight, etc.

The invention still further relates to a nutritional composition comprising betaine and advantageously one or more carbohydrates for ensuring that at the time of surgery, the patient is in an anabolic rather than a catabolic state, has loaded glycogen stores, and has an 'empty' stomach. This regimen has been proven to result in less thirst, hunger and anxiety before the operation, a reduction in postoperative insulin resistance, an improved postoperative sense of well being and a preservation of lean body mass. This can lead to shorter hospital stays, bringing benefits for both the patient and healthcare costs. Such a composition comprises advantageously more than 0.5% by weight betaine (especially glycine betaine), preferably more than 1% by weight betaine (especially glycine betaine), most preferably between 2% and 20% by weight betaine (glycine betaine), such as 3% by weight, 5% by weight, 7% by weight, 10% by weight, 12% by weight, 15% by weight, 18% by weight. Higher betaine content is possible in specific case, such as 25% by weight, 35% by weight, etc.

The invention still further relates to a nutritional composition comprising betaine for patients with diabetes, so as to reduce hyper/hypoglycaemic states in addition to general improvements of nutritional status. The composition further comprises advantageously at least a compound selected from the group consisting of fat, monounsaturated fatty acids, enriched with fibers and micronutrients, such as antioxidants, and mixtures thereof. Such a composition comprises advantageously more than 0.5% by weight betaine (especially glycine betaine), preferably more than 1% by weight betaine (especially glycine betaine), most preferably between 2% and 20% by weight betaine (glycine betaine), such as 3% by weight, 5% by weight, 7% by weight, 10% by weight, 12% by weight, 15% by weight, 18% by weight. Higher betaine content is possible in specific case, such as 25% by weight, 35% by weight, etc The invention still further relates to a nutritional composition comprising betaine for treating renal failure. Renal failure implies mainly the failure of renal excretory function. This is accompanied to a variable extent by failure of erythropoietin production, vitamin D activation, and regulation of acid-base balance, regulation of salt and water balance and blood pressure.

The composition further comprises advantageously Protein or/and fat composition advantageously with a high proportion of mono-unsaturated fatty acids and low proportions of saturated and poly-unsaturated fatty acids. Such a composition comprises advantageously more than 0.5% by weight betaine (especially glycine betaine), preferably more than 1% by weight betaine (especially glycine betaine), most preferably between 2% and 20% by weight betaine (glycine betaine), such as 3% by weight, 5% by weight, 7% by weight, 10% by weight, 12% by weight, 15% by weight, 18% by weight. Higher betaine content is possible in specific case, such as 25% by weight, 35% by weight, etc The invention further relates to a Glutafin gluten-free nutritional composition comprising betaine, said composition further comprising calcium and fiber, said composition helping individuals suffering from celiac disease, and enabling said individuals to increase their calcium and fiber intake, thus minimising the risk of developing osteoporosis and helping to prevent constipation. Such a composition comprises advantageously more than 0.5% by weight betaine (especially glycine betaine), preferably more than 1% by weight betaine (especially glycine betaine), most preferably between 2% and 20% by weight betaine (glycine betaine), such as 3% by weight, 5% by weight, 7% by weight, 10% by weight, 12% by weight, 15% by weight, 18% by weight. Higher betaine content is possible in specific case, such as 25% by weight, 35% by weight, etc.

These and other aspects of the invention are described in greater detail below, as well as in the claims.

DETAILED DESCRIPTION OF THE INVENTION

The invention is useful whenever it is desirable to increase constitutive Nitric Oxide Synthase (Platelet, Type I & Type III isoform) activity in a cell, in a tissue, in an organ, in the blood, in bodily fluids or in a subject. A subject as used herein includes humans, non human primates, dogs, cats, sheep, goats, cows, pigs, horses and rodents. The invention thus is useful for therapeutic purposes and also is useful for research purposes such as in testing in animal or in vitro models of medical, physiological or metabolic pathways or conditions. Nitric Oxide Synthase is the enzyme that catalyzes the reaction that produces nitric oxide from the substrate L-arginine. As the names imply, endothelial cell nitric oxide Synthase (NOS) refers to the Type III isoform of the enzyme found in the endothelium, Type I refers to Brain or neuronal NOS found in the brain, Platelet NOS refers to NOS expressed in platelets. These 3 constitutive forms are calcium dependant. The inducible form iNOS is calcium independent is excluded.

There are two general forms of NOS: constitutive and inducible. NO is continuously produced by constitutive NO synthase (cNOS). The cNOS found in endothelial cells is also referred as eNOS, NOS, or Type III NOS. The activity of cNOS is modulated by calcium that is released from subsarcolemmal storage sites in response to the binding of certain ligands to their receptors. Substances such as acetylcholine, bradykinin, histamine, insulin, and substance P stimulate NO production by this mechanism. Another important mechanism regulating the release of NO is shearing forces acting on the luminal surface of vascular endothelium. By this mechanism, increased flow velocity stimulates calcium release and increased cNOS activity. The inducible form of NOS (iNOS, or Type II NOS) is not calcium-dependent, but instead is stimulated by the actions of cytokines (e.g., tumour necrosis factor, interleukins) and bacterial endotoxins (e.g., lipopolysaccharide). Induction of iNOS occurs over several hours and results in NO production that may be more than a 1,000-fold greater than that produced by cNOS. This is an important mechanism in the pathogenesis of inflammation.

By "NOS activity", it is meant the ability of a cell to generate nitric oxide from the substrate L-arginine. Increased NOS activity can be accomplished in a number of different ways. For example, an increase in the amount of NOS protein or an increase in the activity of the protein (while maintaining a constant level of the protein) can result in increased "activity". An increase in the amount of protein available can result from increased transcription of the NOS gene, increased stability of the NOS mRNA or a decrease in NOS protein degradation. (The term "expression" is used interchangeably with the term "activity" throughout this application).

The NOS activity in a cell, in an organ such as blood or in a tissue can be measured in a variety of different ways. A direct measure would be to measure the amount of NOS present. Another direct measure would be to measure the amount of conversion of arginine to citrulline by NOS or the amount of generation of nitric oxide by NOS under particular conditions, such as the physiologic conditions of the tissue. The NOS activity also can be measured more indirectly, for example by measuring mRNA half-life (an upstream indicator) or by a phenotypic response to the presence of nitric oxide (a downstream indicator). One phenotypic measurement employed in the art is detecting endothelial dependent relaxation in response to acetylcholine, which response is affected by NOS activity. The level of nitric oxide present in a sample can be measured using a nitric oxide meter. All of the foregoing techniques as the Griess reaction are well known to those of ordinary skill in the art.

The present invention, by causing an increase in NOS activity, permits not only the re-establishment of normal base-fine levels of NOS activity, but also allows increasing such activity above normal base-line levels. Normal base-line levels are the amounts of activity in a normal control group, controlled for age and having no symptoms which would indicate alteration of endothelial cell Nitric Oxide Synthase activity (such as hypoxic conditions, hyperlipidaemia and the like). The actual level then will depend upon the particular age group selected and the particular measure employed to assay activity. Specific examples of various measures are provided below. In abnormal circumstances, e.g. hypoxic conditions, pulmonary hypertension, etc., endothelial cell Nitric Oxide Synthase activity is depressed below normal levels. Surprisingly, when using betaine according to the invention, not only can normal base-line levels be restored in such abnormal conditions, but endothelial cell Nitric Oxide Synthase activity can be increased desirably far above normal base-line levels of endothelial cell Nitric Oxide Synthase activity. Thus, "increasing activity" means any increase in endothelial cell Nitric Oxide Synthase activity in the subject resulting from the treatment with betaine according to the invention, including, but not limited to, such activity as would be sufficient to restore normal base-line levels and such activity as would be sufficient to elevate the activity above normal base-line levels.

According to the present invention betaine administration increases NO levels in subjects in need. Nitric Oxide Synthase activity is involved in many conditions, including stroke, pulmonary hypertension, impotence, heart failure, gastric and oesophageal motility disorders, kidney disorders such as kidney hypertension and progressive renal disease, insulin deficiency, hypoxia-induced conditions, glaucoma, etc. Thus betaine administration treats such pathologic conditions. In one embodiment of the invention the decrease in endothelial cell Nitric Oxide Synthase activity is cytokine induced. Cytokines are soluble polypeptides produced by a wide variety of cells that control gene activation and cell surface molecule expression. They play an essential role in the development of the immune system and thus in the development of an immune response. However, besides their numerous beneficial properties, they have also been implicated in the mechanisms for the development of a variety of inflammatory diseases. For example, the cytokines TNF-a and IL-1 are thought to be part of the disease causing mechanism of non-cholesterol induced atherosclerosis, transplant arterial sclerosis, rheumatoid arthritis, lupus, scleroderma, emphysema, asthma, allergy, etc. Subjects of such disorders exhibit lower levels of endothelial cell Nitric Oxide Synthase activity (which is thus "cytokine induced"), and may benefit from therapy using the agents of the present invention.

Diabetic angiopathy is the main cause of morbidity and mortality in patients with diabetes mellitus. Clinical manifestations and pathophysiological mechanisms of diabetic angiopathy can be traced back to the development of endothelial cell dysfunction with alterations in the eNOS/NO system production or availability as the primum movens in its natural history. Hyperglycemia per se or through the accumulation of AGEs, increased oxidative stress, leading to NOS uncoupling and NO-quenching by excess superoxide and peroxynitrite, and individual genetic background are thought to be responsible for this NO metabolism imbalance.

Hence, abnormality in NO availability results in generalized accelerated atherosclerosis, hyperfiltration, glomerulosclerosis, tubulointerstitial fibrosis and progressive decline in glomerular filtration rate, and apoptosis and neovascularization in the retina. Indeed, the parallel development of nephropathy, retinopathy, and macro-angiopathy may be considered as manifestations of endothelial dysfunction at distinct vascular sites. According to the present invention are claimed the uses of betaine to treat such diabetic conditions, pathologies and NO unbalances.

One important embodiment of the invention is treatment of ischemic stroke. Ischemic stroke (ischemic cerebral infarction) is an acute neurological injury that results from a decrease in the blood flow involving the blood vessels of the brain. Ischemic stroke is divided into two broad categories, thrombotic and embolic.

A surprising finding was made in connection with the treatment of ischemic stroke. In particular, it was discovered that treatment according to the invention can reduce the brain injury that follows an ischemic stroke. Brain injury reduction, as demonstrated in the examples below, can be measured by determining a reduction in infarct size in the treated versus the control groups. Likewise, functional tests measuring neurological deficits provided further evidence of reduction in brain injury in the treated animals versus the controls. Cerebral blood flow should also be better in the treated animals versus the controls. Thus, in the various accepted models of brain injury following stroke, positive effects could be observed in the treated animals versus the control animals. It is believed that all of the foregoing positive results are attributable to the up-regulation of endothelial cell Nitric Oxide Synthase activity following Rose Bengal free radicals induced brain injury.

An important embodiment of the invention is the treatment of a subject with an abnormally elevated risk of an ischemic stroke. As used herein, subjects having an abnormally elevated risk of an ischemic stroke are a category determined according to conventional medical practice. This category includes, for example, subjects which are having elected vascular surgery. Typically, the risk factors associated with cardiac disease are the same as are associated with stroke. The primary risk factors include hypertension, hypercholesterolemia, and smoking. In addition, atrial fibrillation or recent myocardial infarctions are important risk factors. According to the invention atrial fibrillation and myocardial infarctions can be treated with the betaines of the invention.

The treatment of stroke can be for patients who have experienced a stroke or can be a prophylactic treatment. If prophylactic, then the treatment is for subjects having an abnormally elevated risk of an ischemic stroke, as described above. If the subject has experienced a stroke, then the treatment can include acute treatment. In one embodiment according to the invention cerebral vasospasm can be treated.

Another important embodiment of the invention is treatment of pulmonary hypertension. Pulmonary hypertension is a disease characterized by increased pulmonary arterial pressure and pulmonary vascular resistance. Hypoxemia, hypocapnia, and an abnormal diffusing capacity for carbon monoxide are almost invariable findings of the disease. Additionally, according to the present invention, patients with pulmonary hypertension also have reduced levels of NOS expression and/or activity in their pulmonary vessels. Additionally, according to the present invention airway diseases, alveolar diseases, asthma, bronchiolitis, cystic fibrosis can be treated by the betaines. Traditionally, the criteria for subjects with, or at risk for pulmonary hypertension are defined on the basis of clinical and histological characteristics according to Heath and Edwards (Circulation, 1958).

Subjects may be treated prophylactically to reduce the risk of pulmonary hypertension or subjects with pulmonary hypertension may be treated long term and/or acutely. If the treatment is prophylactic, then the subjects treated are those with an abnormally elevated risk of pulmonary hypertension. A subject with an abnormally elevated risk of pulmonary hypertension is a subject with chronic exposure to hypoxic conditions, a subject with sustained vasoconstriction, a subject with multiple pulmonary emboli, a subject with cardiomegaly and/or a subject with a family history of pulmonary hypertension. Another important embodiment of the invention involves treating hypoxia-induced conditions with betaine. Hypoxia as used herein is defined as the decrease below normal levels of oxygen in a tissue. Hypoxia can result from a variety of circumstances, but most frequently results from impaired lung function. Impaired lung function can be caused by emphysema, cigarette smoking, chronic bronchitis, asthma, infectious agents, pneumonitis (infectious or chemical), lupus, rheumatoid arthritis, inherited disorders such as cystic fibrosis, obesity, alpha sub.1-antitrypsin deficiency and the like. It also can result from non-lung impairments such as from living at very high altitudes. Hypoxia can result in pulmonary vasoconstriction via inhibition of NOS activity. In one embodiment nebulization dosage form comprising a betaine as therapeutically active agent for treating severe pulmonary arterial hypertension (PAH) is described.

Another important embodiment of the invention is the treatment of heart failure with betaine. Heart failure is a clinical syndrome of diverse aetiologies linked by the common denominator of impaired heart pumping and is characterized by the failure of the heart to pump blood commensurate with the requirements of the metabolizing tissues, or to do so only from an elevating filling pressure. In one embodiment according to the invention the betaines can serves as treatment in stable angina, unstable angina & coronary syndromes. In medically treated hypertensive patients with micro-vascular angina, oral betaine may represent a useful therapeutic option.

According to the invention betaine administration can prolong ventricular repolarisation through nitric oxide release in heart.

Endothelial dysfunction defined as the impaired ability of vascular endothelium to stimulate vasodilatation plays a key role in the development of atherosclerosis and in various pathological conditions which predispose to atherosclerosis, such as hypercholesterolemia, hypertension, type 2 diabetes and chronic renal failure. The major cause of the endothelial dysfunction is decreased bioavailability of nitric oxide (NO); a potent biological vasodilator produced in vascular endothelium from L-arginine by the endothelial NO synthase (eNOS). In vascular diseases, the bioavailability of NO can be impaired by various mechanisms, including decreased NO production by eNOS, and/or enhanced NO breakdown due to increased oxidative stress. The deactivation of eNOS is often associated with elevated plasma levels of its endogenous inhibitor, NG NG-dimethyl-L-arginine (ADMA).

In hypercholesterolemia, a systemic deficit of NO may also increase the levels of low density lipoproteins (LDL) by modulating its synthesis and metabolism by the liver, as suggested by recent in vivo and in vitro studies using organic NO donors. Therapeutic strategies aiming to reduce the risk of vascular diseases by increasing bioavailability of NO continue to be developed. Cholesterol lowering drugs, statins, have been shown to improve endothelial function in patients with hypercholesterolemia and atherosclerosis. Promising results were also obtained in some, but not all, vascular diseases after treatment with antioxidant vitamins (C and E) and after administration of eNOS substrate, L-arginine, or its cofactor, tetrahydrobiopterin (BH4). Novel therapeutic strategies are claimed in the present specification. Such treatment strategies which may produce beneficial changes in the vascular endothelium include the above mentioned treatments in combination with the use of a betaine as NOS up-regulating agent. In one embodiment the betaines can be used alone for these purposes.

Platelets play an important role in physiologic haemostasis and pathologic thrombosis that complicate the course of vascular disorders, A number of platelet functions including adhesion, aggregation and recruitment are controlled by nitric oxide (NO) generated by platelets and the endothelial cells. Derangements in this generation may contribute to the pathogenesis of thrombotic complications of vascular disorders. The pharmacologic supplementation of the diseased vasculature with drugs releasing NO, such as betaine, will help to restore the haemostatic balance.

Nitric Oxide Released from activated platelets inhibits platelet recruitment. Adhesion of platelets to the vessel wall is prevented, in part, by endothelial cells production of nitric oxide (NO). Nitric oxide also inhibits platelet aggregation and prevents thrombosis endotoxins induced glomerular damage. The normal activation-dependent increase in platelet surface glycoprotein expression, including P selectin, actins, the activated glycoprotein IIb-IIIa complex are also inhibited by NO. Thus betaine effect on NO is beneficial in related adhesion pathologies as on related sites of actions.

A constitutive nitric oxide synthase (cNOS) has been identified in megakaryoblastic cells thus betaine might be beneficial in pathologic situations where such cells might be involved.

Nitric oxide is also produced within the context of platelet aggregation, inhibition of leukocyte-endothelial interactions and smooth muscle cell proliferation where betaine administration can exercises beneficial and therapeutical effects.

Nitric oxide enhances wound healing in diabetes which can be triggered, augmented, maintained or shortened by betaine treatment.

Besides blood pressure, betaine, optionally in combination with L-Arginine, via enhancement of nitric oxide synthesis in endothelium activates intra-platelet guanylate cyclase, thus increasing cGMP concentration, and preventing platelet adhesion and aggregation and by the way preventing coronary arterial diseases expressions.

Betaines-induced inhibition of Na, K-ATPase activity correlated with increases in cGMP Betaines-induced inhibition of Na, K-ATPase activity involves muscarinic receptor activation. It involves activation soluble guanylate cyclase and stimulation of cGMP—Cyclic guanosine monophosphate (cGMP) is a cyclic nucleotide derived from guanosine triphosphate (GTP). cGMP acts as a second messenger much like cyclic AMP, most notably by activating intracellular protein kinases in response to the binding of membrane-impermeable peptide hormones to the external cell surface.

Cyclic nucleotide phosphodiesterases (PDE 1-6) degrade cGMP by hydrolyzing cGMP into 5'-GMP. Phosphodiesterase inhibitors prevent the degradation of cGMP, thereby enhancing and/or prolonging its effects. For example, Sildenafil (Viagra®) enhances the vasodilatory effects of cGMP within the corpus cavernosum by inhibiting PDE S (or PDE V). This is used as a treatment for erectile dysfunction. In the present invention the betaines are claimed to possess the same pharmacological properties than phosphodiesterase inhibitors by preventing the degradation of cGMP and thereby enhancing and/or prolonging its effects.

In one embodiment by augmenting NO levels betaine can favourably act on erectile function. Erectile dysfunction is defined as the "inability of the male to achieve or maintain an erection sufficient for sexual intercourse." Erectile dysfunction (formerly called impotence) is not a new problem. The earliest written reference to impotence dates from the eighth century BC in India and several references are included in the Bible. Neurogenic nitric oxide is still to considered the most important factor for immediate relaxation of penile vessels and corpus cavernosum; according to the present invention betaines are claimed to augment neurogenic nitric oxide in the living body. Betaine by enhancing nitric oxide (NO) mediates penile erection, the endothelial isoform of NO synthase (eNOS) has been implicated in this function which is a phosphodiesterase 5 inhibitor, increasing the persistence of cyclic guanosine monophosphate and thereby enhancing erectile response.

Nitric oxide (NO) is produced by vascular endothelium and smooth muscle, cardiac muscle, and many other cell types. Thus according to the invention betaine by augmenting Nitric oxide serves positively, i.e. prevents/treats, many important functions in the cardiovascular system as listed below:

Vasodilation (ligand mediated and flow dependent)

Inhibition of vasoconstrictor influences (e.g., inhibits angiotensin II and sympathetic vasoconstriction)

Inhibition of platelet adhesion to the vascular endothelium (anti-thrombotic)

Inhibition of leukocyte adhesion to vascular endothelium (anti-inflammatory)

Antiproliferative (e.g., inhibits smooth muscle hyperplasia following vascular injury)

Scavenging superoxide anion (anti-inflammatory)

The mechanism of many of these actions on NO involves the formation of cGMP. When NO is formed by an endothelial cell, it readily diffuses out of the cell and into adjacent smooth muscle cells where is binds to a heme moiety on guanylyl cyclase and activates this enzyme to produce cGMP from GTP. Increased cGMP activates a kinase that subsequently leads to the inhibition of calcium influx into the smooth muscle cell, and decreased calcium-calmodulin stimulation of myosin light chain kinase (MLCK). This in turn decreases the phosphorylation of myosin light chains, thereby decreasing smooth muscle tension development and causing vasodilation. Increases in cGMP lead to myosin light chain dephosphorylation by activating the phosphatase. The anti-platelet aggregatory effects of NO are also related to the increase in cGMP. Drugs that inhibit the breakdown of cGMP (inhibitors of cGMP-dependent phosphodiesterase such as Sildenafil [Viagra]) potentiate the effects of NO-mediated actions on the target cell. Thus the betaines of the invention possess the same properties as the same cGMP increasing effects and NO-mediated actions on the target cells, tissues and organs. Thus betaines administration are claimed to augment cGMP in the living body.

When NO production is impaired as occurs when the vascular endothelium becomes damaged or dysfunctional, the following can result:

Vasoconstriction (e.g., coronary vasospasm, elevated systemic vascular resistance, hypertension)
Platelet aggregation and adhesion leading to thrombosis
Up-regulation of leukocyte and endothelial adhesion molecules leading to enhanced inflammation
Vascular stenosis, or restenosis as occurs following balloon angioplasty and stent placement
Increased inflammation and tissue damage mediated by reactive oxygen species such as superoxyde anion and hydroxyl radical Thus according to the present invention betaine administration re-establish NO balance/production and by the way exercises a therapeutically beneficial action on these pathologies.

In one embodiment, the beneficial therapeutic effects of the betaines can be used in the treatment of the following diseases/conditions which are associated with endothelial dysfunction and reduced NO production and/or bioavailability:

Hypertension
Obesity
Dyslipidemias
Diabetes (both type I and II)
Heart failure
Atherosclerosis, cigarette smoking, aging, and vascular injury In one embodiment, the beneficial therapeutic effects of the betaines is linked to the inhibition or the decreased of endothelin expression. Based clinical trial data, the endothelin axis is emerging as potentially important in the biology of prostate cancer. Androgen refractory prostate cancer continues to evade effective treatment. The potent vasoconstrictor endothelin-1 is produced by prostate cancer and appears to have a role in prostate cancer progression and morbidity, thus the betaines of the invention are claimed to be therapeutically beneficial in such diseases. Optionally the betaine can be combined to anti-cancerous agents, optionally enhancing their therapeutically effects, when facilitating their delivery (anti-cancerous agents) at the aimed sites. The betaines are claimed to lower endothelin-1 (ET-1) levels in a living body and by the way to treat endothelin related diseases or counteract endothelin activity.

For instance endothelin inhibition improves cerebral blood flow and is neuroprotective in pneumococcal meningitis, thus betaine administration is beneficial. It can be also used in unilateral urethral obstruction.

In one embodiment the betaines, according to the invention, are claimed to augment the level of NO in Alzheimer's disease (AD) and by the way alleviating a series of microvascular ischemic events in the brain, notably in the medial temporal lobe. By augmenting level of cerebral NO in Alzheimer's disease the betaines trigger vasodilation in the brain and better blood circulation. These beneficial effects of betaine in brain circulation can also be therapeutic in vascular dementia and In one embodiment the betaines of the invention are claimed to treat potential acquired deficiency indications such as severe burns, coronary artery bypass graft surgery, disseminated intravascular coagulation and sepsis.

In one embodiment the betaines are claimed to augment the role of NO in nerve injury-induced tactile allodynia, by enhancing neuronal NO synthase (nNOS) expression in the spinal cord and dorsal root ganglia. Furthermore betaine can augment functional role for spinal nitric oxide (NO) in the modulation of thermal and/or inflammatory hyperalgesia.

Thus betaine eNOS-derived NO will play an important beneficial role in limiting cerebral venular leukocyte adhesion Up-regulation of eNOS by betaines in vivo can also serves as treatment in hypoxia, hypoxic pulmonary hypertension, contractile dysfunction induced by bladder outlet obstruction potential treatment of urinary incontinence, Alzheimer's disease (AD) and the prevention and treatment of accelerated bone resorption associated with disorders such as osteoporosis, inflammatory joint disease and Paget's disease.

In one embodiment, the betaines counteract a loss of endothelial-derived NO activity which may contribute to the atherogenic process. For example, endothelial-derived NO inhibits several components of the atherogenic process including monocytes adhesion to the endothelial surface, adhesiveness of aortic endothelium for monocytes, platelet aggregation, vascular smooth muscle cell adhesion and vasoconstriction.

In addition, NO can prevent oxidative modification of low-density lipoprotein (LDL), which is a major contributor to atherosclerosis particularly in its oxidized form. The levels of superoxide and oxidized LDL can be decreased by administering betaines.

In one embodiment betaine protects NO in the body (blood) from superoxyde $O_2^-$ oxidation to peroxynitrite ($ONOO^-$).

In one embodiment the betaine are claimed to act as vasodilators. For example vasodilators represent one of the main steps for the medical treatment of pulmonary hypertension. Calcium blockers, the only drugs active when administered orally, provide a satisfactory clinical response in 25-30% of treated patients. Prostaglandins are active in a higher percentage of patients and can be infused in a domiciliary regimen with portable pumps even for long periods of time. Nitric oxide is the only selective pulmonary vasodilator, it is used in pediatric and adult cardiac surgery and in patients affected by respiratory distress syndrome, but its use is restricted to intensive care units and many cautions must be adopted. Betaine being orally effective could be the treatment of choice for these pathologies. In one embodiment the betaines can be combined in pharmaceutical combination/treatment comprising a betaine and endothelin inhibitors, cGMP phosphodiesterase inhibitors, prostaglandins, calcium blockers, etc.

People with sickle-cell disease are also at high risk of other complications, especially stroke. There are few effective treatments for the disease, and most have serious side effects. Acute chest syndrome characterized by chest pain, fever, high blood pressure in the lungs, and a chest X ray showing clogged or collapsed lungs—is the most life-threatening complication of sickle-cell disease.

The syndrome generally strikes children. Betaine is claimed to be beneficial in these pathologies.

In one embodiment the betaines are claimed to act as agonists to constitutive NO synthases and to NO production.

In one embodiment of the invention, the betaines are claimed to act synergically with Angiotensin-converting enzyme (ACE) inhibitors, such as captopril, fosinopril, enalapril, ceronapril, lisinopril and the like, and angiotensin II antagonists such as losartan, irbesartan, valsartan, candesartan, tasosartan and eprosartan, as to enhance constitutive nitric oxide production and by the way to potentialises their use as vasodilating cardiovascular agents in treating high blood pressure and congestive heart failure.

In one embodiment of the invention, the betaines are claimed to act synergically with Nitrates such as isosorbide dinitrate, isosorbide mononitrate and nitroglycerin, as to enhance constitutive nitric oxide production and by the way to potentialises their coronary and peripheral vasodilating effect in the prevention and treatment of angina pectoris.

The present invention relates to the pharmaceutical uses of betaines for up-regulating, enhancing, stimulating, controlling and/or increasing constitutive nitric oxide synthase expression and endogenous nitric oxide production in a mammal, particularly in a human. Additionally, the betaines are claimed to augment after administration both immunological and functional (activity) expressions of Tissue Factor Pathway Inhibitor (TFPI) in a mammal, particularly in a human.

The present invention relates to the pharmaceutical uses of betaines for up-regulating, enhancing, stimulating, controlling and/or increasing constitutive nitric oxide synthase expression and endogenous nitric oxide production in a mammal, particularly in a human.

In one embodiment the betaine are claimed to lower erythrocytes sequestration in malaria pathologies.

According to an aspect of the invention, a method is provided for increasing endothelial cell Nitric Oxide Synthase activity in a subject to treat a condition favorably affected by an increase in endothelial cell Nitric Oxide Synthase activity in a tissue. The method involves administering to a subject in need of such treatment a betaine in an amount effective to increase endothelial cell Nitric Oxide Synthase activity in the tissue of the subject and or augment TFPI production is a subject. Such activities being particularly suitable in malaria and leishmaniasis related pathologies. In one embodiment the betaines can be simultaneously administered with anti malarial compounds.

Betaines can also be used alone and in combination with an ACE inhibitor in control of blood pressure, metabolism and other endpoints in hypertensive patients, diabetic hypertensive patients, as in renal patients.

Due to their constant positive charge the betaines of the invention are expected to have electrostatic binding to the platelet phospholipids, phosphatidylinositol and phosphatidylserine exerting regulating action, antagonistic, agonistic and/or inhibiting action on these sites. By the way betaines, preferably glycine betaine (n=1 in the general formula), exert regulating action or inhibiting action on the prothrombinase complex and activation of prothrombin to thrombin. In a particular embodiment betaines could be beneficial in related pathologies linked to various negatively charged phospholipids in a mammal.

In essential hypertension, reduced activity of NO could also be explained by inactivation of NO through the increased superoxide production. Under these pathological conditions, the generation of superoxide anion is dependent on cyclooxygenases and possibly also NAD(P)H oxidases. In hypertensive patients, inhibition of cyclooxygenase with indomethacin resulted in augmentation of the vasodilatory response. Betaine alone or in combination with indomethacin is claimed to have beneficial effects. Such synergistic combinations with betaines for treating/alleviating/preventing essential hypertension can be extended to all other hypertension lowering active drugs.

Nitric Oxide Synthase activity is involved in many conditions, including stroke, arterial diseases, chronic venous insufficiency, syndrome X, high pulmonary vascular resistance, pulmonary hypertension after reoxygenation with cardiopulmonary bypass, restenosis after stent placement, restenosis after stent balloon angioplasty, restenosis, myocardial ischemia-reperfusion damage, cardiac infarction, myocardial infarction, syndrome X, insulin resistance, diabetic angiopathy, ischemia reperfusion injuries, leg ulcers, pneumonia, pulmonary hypertension, impotence, heart failure, angina, unstable angina, gastric and oesophageal motility disorders, gastric and oesophageal healing, healing, kidney disorders such as kidney hypertension and progressive renal disease, asthma, insulin deficiency and hypoxia-induced conditions, thus betaines have therapeutically beneficial effects on these pathologies by up-regulating constitutive nitric oxide levels.

In an other embodiment the betaines of the invention, due to their activity either on constitutive nitric oxide and/or Tissue Factor Pathway Inhibitor, are claimed to treat or to provide a method of treatment of pathological conditions such as Idiopathic Thrombocytopenic Purpura, Purpura, thrombocytopenia, sepsis, psoriasis, inflammation, impaired immune function, malaria, cystic fibrosis, polyps, nasal polyps, portal hypertension cardiovascular diseases, atherosclerosis, hypertension, diabetes, cardiac diseases, atrial fibrillation, blood coagulation troubles, Raynaud's disease, Alzheimer disease, vascular dementia, Parkinson disease, memory troubles, intermittent claudication, blood circulation troubles, legs circulation troubles, peripheral arterial disease, peripheral arterial occlusive disease, haemodialysis troubles, renal diseases, liver diseases, metabolic syndrome, syndrome X, ocular troubles, pulmonary hypertension, angina pectoris, stroke, scleroderma, deep venous thrombosis, air travel troubles, bleeding troubles, cancer, cancer therapy, chemotherapy, restinosis, stent restinosis, inflammation, endothelial dysfunction, sexual dysfunctions, haemorrhoids, fatigue, pneumonia, asthma, trauma, surgery, inflammation, sub-fertility, lactation problems, gut disorders, arthritis and other joint problems, ageing, impaired immune function, burns, malaria, cystic fibrosis, tuberculosis, migraine, neurological problems, schizophrenia, depression, respiratory infections, HIV, muscle soreness, drug adduction and drug intoxication.

The invention relates also to a method of treatment of various one or more troubles, to a composition for said treatment (the composition comprising an effective amount of betaine, in particular glycine betaine), to a method for the preparation of such a composition, in which troubles is a trouble selected from the group consisting of:

Idiopathic Thrombocytopenic Purpura troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Purpura, thrombocytopenia troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Sepsis troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Psoriasis diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Inflammation diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Impaired immune function diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Malaria diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Cystic fibrosis diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Polyps diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Nasal polyps diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Portal hypertension cardiovascular diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Atherosclerosis diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Hypertension diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Diabetic diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Cardiac diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Atrial fibrillation diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Blood coagulation diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Raynaud's disease or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Alzheimer disease or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Vascular dementia diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Parkinson disease or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Memory diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Intermittent claudication diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Blood circulation diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Legs circulation disease or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Peripheral arterial diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Peripheral arterial occlusive diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Haemodialysis diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Renal diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Liver diseases troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Metabolic syndrome diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Syndrome X diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Ocular diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Pulmonary hypertension diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Angina pectoris diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Stroke diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Scleroderma diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Deep venous thrombosis diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Air travel diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Bleeding diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Cancer diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, cancer therapy troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, chemotherapy troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Restinosis diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Stent restinosis diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Inflammation diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Endothelial dysfunction diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Sexual dysfunctions diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Haemorrhoids diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Fatigue diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Pneumonia diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Asthma diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Trauma diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Surgery diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Sub-fertility diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Lactation diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Gut diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Arthritis diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Joint problem diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Ageing diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Impaired immune function diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Burns diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Cystic fibrosis diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Tuberculosis diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Migraine diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Neurological problems diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Schizophrenia diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Depression diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Respiratory infections diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, HIV diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Muscle soreness diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, Drug intoxication or adduction diseases or troubles caused by a nitric oxide deficiency, in particular a constitutive nitric oxide deficiency and/or neural nitric oxide deficiency and/or platelet nitric oxide deficiency and/or c nitric oxide deficiency and/or Type III nitric oxide deficiency and/or endogenous nitric oxide deficiency, and combinations thereof.

The invention further relates to a method of treatment of various one or more troubles or diseases, to a composition for said treatment (the composition comprising an effective amount of betaine, in particular glycine betaine), to a method for the preparation of such a composition, in which troubles is a trouble or disease selected from the group consisting of Idiopathic Thrombocytopenic Purpura diseases or troubles caused by Tissue Factor Pathway Inhibitor (TFPI) deficiency, Thrombocytopenia troubles caused by Tissue Factor Pathway Inhibitor (TFPI) deficiency, Sepsis troubles caused by Tissue Factor Pathway Inhibitor (TFPI) deficiency, Psoriasis diseases or troubles caused by Tissue Factor Pathway Inhibitor (TFPI) deficiency, Inflammation diseases or troubles caused by Tissue Factor Pathway Inhibitor (TFPI) deficiency, Impaired immune function diseases or troubles caused by Tissue Factor Pathway Inhibitor (TFPI) deficiency, Malaria diseases or troubles caused by Tissue Factor Pathway Inhibitor (TFPI) deficiency, Cystic fibrosis diseases or troubles caused by Tissue Factor Pathway Inhibitor (TFPI) deficiency, Polyps diseases or troubles caused by Tissue Factor Pathway Inhibitor (TFPI) deficiency, Nasal polyps diseases or troubles caused by Tissue Factor Pathway Inhibitor (TFPI) deficiency, Portal hypertension cardiovascular diseases or troubles caused by Tissue Factor Pathway Inhibitor (TFPI) deficiency, Atherosclerosis diseases or troubles caused by Tissue Factor Pathway Inhibitor (TFPI) deficiency, Hypertension diseases or troubles caused by Tissue Factor Pathway Inhibitor (TFPI) deficiency, Diabetic diseases or troubles caused by Tissue Factor Pathway Inhibitor (TFPI) deficiency, Cardiac diseases or troubles caused by Tissue Factor Pathway Inhibitor (TFPI) deficiency, Atrial fibrillation diseases or troubles caused by Tissue Factor Pathway Inhibitor (TFPI) deficiency, Blood coagulation diseases or troubles caused by Tissue Factor Pathway Inhibitor (TFPI) deficiency, is Raynaud's disease or troubles caused by Tissue Factor Pathway Inhibitor (TFPI) deficiency, Alzheimer disease or troubles caused by Tissue Factor Pathway Inhibitor (TFPI) deficiency, Vascular dementia diseases or troubles caused by Tissue Factor Pathway Inhibitor (TFPI) deficiency, Parkinson disease or troubles caused by Tissue Factor Pathway Inhibitor (TFPI) deficiency, Memory diseases or troubles caused by Tissue Factor Pathway Inhibitor (TFPI) deficiency, Intermittent claudication diseases or troubles caused by Tissue Factor Pathway Inhibitor (TFPI) deficiency, Blood circulation diseases or troubles caused by Tissue Factor Pathway Inhibitor (TFPI) deficiency, Legs circulation disease or troubles caused by Tissue Factor Pathway Inhibitor (TFPI) deficiency, Peripheral arterial diseases or troubles caused by Tissue Factor Pathway Inhibitor (TFPI) deficiency, Peripheral arterial occlusive diseases or troubles caused by Tissue Factor Pathway Inhibitor (TFPI) deficiency, Haemodialysis diseases or troubles caused by Tissue Factor Pathway Inhibitor (TFPI) deficiency, Renal diseases or troubles caused by Tissue Factor Pathway Inhibitor (TFPI) deficiency, Liver diseases troubles caused by Tissue Factor Pathway Inhibitor (TFPI) deficiency, Metabolic syndrome diseases or troubles caused by Tissue Factor Pathway Inhibitor (TFPI) deficiency, Syndrome X diseases or troubles caused by Tissue Factor Pathway Inhibitor (TFPI) deficiency, Ocular diseases or troubles caused by Tissue Factor Pathway Inhibitor (TFPI) deficiency, Pulmonary hypertension diseases or troubles caused by Tissue Factor Pathway Inhibitor (TFPI) deficiency, Angina pectoris diseases or troubles caused by Tissue Factor Pathway Inhibitor (TFPI) deficiency, Stroke diseases or troubles caused by Tissue Factor Pathway Inhibitor (TFPI) deficiency, Scleroderma diseases or troubles caused by Tissue Factor Pathway Inhibitor (TFPI) deficiency, Deep venous thrombosis diseases or troubles caused by Tissue Factor Pathway Inhibitor (TFPI) deficiency, Air travel diseases or troubles caused by Tissue Factor Pathway Inhibitor (TFPI) deficiency, Bleeding diseases or troubles caused by Tissue Factor Pathway Inhibitor (TFPI) deficiency, Cancer diseases or troubles caused by Tissue Factor Pathway Inhibitor (TFPI) deficiency, Chemotherapy troubles caused by Tissue Factor Pathway Inhibitor (TFPI) deficiency, Restinosis diseases or troubles caused by Tissue Factor Pathway Inhibitor (TFPI) deficiency, Stent restinosis diseases or troubles caused by Tissue Factor Pathway Inhibitor (TFPI) deficiency, Inflammation diseases or troubles caused by Tissue Factor Pathway Inhibitor (TFPI) deficiency, Endothelial dysfunction diseases or troubles caused by Tissue Factor Pathway Inhibitor (TFPI) deficiency, Haemorrhoids diseases or troubles caused by Fatigue diseases or troubles caused by Tissue Factor Pathway Inhibitor (TFPI) deficiency, Pneumonia diseases or troubles caused by Tissue Factor Pathway Inhibitor (TFPI) deficiency, Asthma diseases or troubles caused by Tissue Factor Pathway Inhibitor (TFPI) deficiency, Trauma diseases or troubles caused by Tissue Factor Pathway Inhibitor (TFPI) deficiency, Surgery diseases or troubles caused by Tissue Factor Pathway Inhibitor (TFPI) deficiency, Arthritis diseases or troubles caused by Tissue Factor Pathway Inhibitor (TFPI) deficiency, Joint problem diseases or troubles caused by Tissue Factor Pathway Inhibitor (TFPI) deficiency, Impaired immune function diseases or troubles caused by Tissue Factor Pathway Inhibitor (TFPI) deficiency, Burns diseases or troubles caused by Tissue Factor Pathway Inhibitor (TFPI) deficiency, Cystic fibrosis diseases or troubles caused by Tissue Factor Pathway Inhibitor (TFPI) deficiency, Tuberculosis diseases or troubles caused by Tissue Factor Pathway Inhibitor (TFPI) deficiency, Migraine diseases or troubles caused by Tissue Factor Pathway Inhibitor (TFPI) deficiency, Neurological diseases or troubles caused by Tissue Factor Pathway Inhibitor (TFPI) deficiency, Schizophrenia diseases or troubles caused by Tissue Factor Pathway Inhibitor (TFPI) deficiency, Depression diseases or troubles caused by Tissue Factor Pathway Inhibitor (TFPI) deficiency, Respiratory infections diseases or troubles caused by Tissue Factor Pathway Inhibitor (TFPI) deficiency, HIV diseases or troubles caused by Tissue Factor Pathway Inhibitor (TFPI) deficiency, Muscle soreness diseases or troubles caused by Tissue Factor Pathway Inhibitor (TFPI) deficiency, Drug intoxication or adduction diseases or troubles caused by Tissue Factor Pathway Inhibitor (TFPI) deficiency, and combinations thereof.

In one embodiment, a method for promoting and/or fastening and/or controlling the healing of a damaged tissue in a patient in need of such treatment, comprising exposing said tissue to a betaine for increasing concentration of nitric oxide, is provided.

Furthermore, it is in the scope of the present invention to describe and claim combinational methods of treatment using betaines and one or more active agents as the pharmaceutical combinations of betaines and one or more active agent selected from the group of:

indomethacin, Sildenafil, citrate salt of Sildenafil, choline, acetylcholine, L-citrulline, NO donors, physiological NO donors, NO precursors, L-arginine, phytochemicals, carotenoids, flavonoids, polyphénols, anthocyans, tetrahydrobiopterin ($BH_4$), organic nitrates acting as synthetic NO donors, organic nitrites acting as synthetic NO donors, Amlodipine, enalapril, alpha-adrenergic blockers, Beta-blockers, angiotensin II antagonists, Vasodilators, Alpha-blockers, Angiotensin antagonists, Alpha-beta-blockers, Alpha-beta-blockers, diuretics, ACE inhibitors, calcium antagonists, endothelin inhibitors, cGMP phosphodiesterase inhibitors, prostaglandins, calcium blockers dietary agents, statins, probucol, antioxidants, vitamins, eNOS substrates, L-arginine, and its cofactor BH4.

In one embodiment the betaines of the invention can be administrated with substances known to be physiological substrates or precursors for NO production, such as L-Arginine. The ratios betaines/L-arginine can vary from 1:10 to 10:1 based on dry weight. The ratios betaines/substrates and/or betaines/precursors can vary from 1:10 to 10:1 based on dry weight. The ratios betaines/precursors can vary from 1:10 to 10:1 based on dry weight.

In one embodiment, the ratios betaines/substrates can vary from 1:100 to 100:1 based on dry weight.

In one embodiment, the ratios betaines/precursors can vary from 1:100 to 100:1 based on dry weight.

In one embodiment the betaines of the invention can be administrated with substances known to be physiological substrates or precursors for NO production, such as L-Arginine. The ratios betaines/L-arginine can vary from 1.100 to 100:1 based on dry weight, preferably between 20:1 and 1:20. The ratios betaines/substrates and/or betaines/precursors can vary from 1:10 to 10:1 based on dry weight. Such a composition comprises advantageously more than 0.5% by weight betaine (especially glycine betaine), preferably more than 1% by weight betaine (especially glycine betaine), most preferably between 2% and 20% by weight betaine (glycine betaine), such as 3% by weight, 5% by weight, 7% by weight, 10% by weight, 12% by weight, 15% by weight, 18% by weight. Higher betaine content is possible in specific case, such as 25% by weight, 35% by weight, etc Such pharmaceutical combinations of betaines and substrates to NO production, such as L-Arginine can be but non limited, oral, parenteral, subcutaneous, transdermal, slow release, controlled release, delayed release dosages forms suitable for oral, parenteral, subcutaneous, transdermal administrations according to different paths. The forms, dosages forms, routes of administrations, techniques, methods of treatment as described in inventor's applications US 20020065320, WO02062322, US 20040033223, WO2004049095, PCT/BE 2004/000053, BE 2004/0364, PCT/BE 2004/00110 are claimed to be suitable in the present invention either for the betaines administrations alone or in the pharmaceutical combinations of betaines and the other compounds described in the present application.

In one embodiment, the pharmaceutical combinations and dosages forms of US 20020065320, WO02062322, US 20040033223, WO2004049095, PCT/BE 2004/000053, BE 2004/0364, PCT/BE 2004/00110 can be combined with the other compounds described in the present application.

The present invention is generally directed to treating a living body, a cell, a tissue, blood or an organ with a mixture of an NO precursor and a betaine which enhances the biotransformation of such precursors into NO.

The present invention is generally directed to treating vessels with a mixture of L-arginine and a betaine which enhances the biotransformation of L-arginine into NO.

Furthermore, it is in the scope of the present invention to describe and claim a composition comprising L-arginine or a physiologically acceptable salt thereof in an amount sufficient to enhance nitric oxide production and at least one betaine that enhances production of nitric oxide or that inhibits degradation of nitric oxide, wherein said composition is in a form suitable for oral administration selected from the group consisting of a pill, tablet, powder, or capsule.

Furthermore, it is in the scope of the present invention to describe and claim a composition comprising an amount of L-arginine effective for enhancing nitric oxide and at least one betaine in an amount sufficient to enhance cGMP, wherein said composition is in a form suitable for oral administration selected from the group consisting of a pill, tablet, powder, or capsule.

Controlled release pharmaceutical compositions of L-arginine, its salts, peptides, and biological equivalents, together with betaines and methods of using the compositions are included.

Furthermore, it is in the scope of the present invention to describe and claim a food product comprising at least one betaine and L-arginine in a combined amount effective to induce and/or to sustain a physiological increase in nitric oxide production in a mammal after ingesting said food product.

Said food products, clinical nutrition products, pharmaceutical compositions, dietary compositions, food compositions and/or nutritional products being particularly useful for ingested and/or enterally administrated nutrition to elderly, hospitalized patients, post surgery patients, injured patients, in bed patients, aged subjects, patients with deficient venous capacitance bed, patients in need for healing, etc.

Another embodiment of the present is to provide pharmaceutical compositions, dietary compositions, food compositions, foods and/or nutritional products comprising at least one betaine and L-arginine in a combined amount effective to induce a physiological increase in nitric oxide production in a mammal after ingesting said food product or composition such ingestion being suitable for preventing and/or treating conditions such as:

Travel related diseases, travel thromboembolism, air travel related diseases, air travel related thromboembolism, blood stagnation in bed patients, intermittent claudication, peripheral arterial diseases, peripheral occlusive arterial diseases, Raynaud's phenomena, and blood problems among menstruating females.

Deep vein thrombosis usually localized in the deep veins of the calf but it can extend into the deep veins of the thigh. The compositions of the invention are suitable to treat/prevent clinical signs such as calf pain and swelling (oedema) of the ankle and possibly calf.

Chronic venous insufficiency is an advanced stage of venous disease caused either by superficial (severe varicose veins) or deep (after deep vein thrombosis) venous pathology and characterized by an increased venous pressure during walking. The main symptoms are pain, swelling of the leg, pigmentation in the ankle area, indurations of skin and even skin breakdown with overt ulceration, such symptoms being treated and/or prevented by the betaines and/or the compositions of the invention.

It is intended by food products, clinical nutrition products, dietary compositions, food compositions and/or nutritional products, products destined to be ingested by mouth such as: food bars, cookies, drinks, energy drinks, confectionaries, gels, chocolate bars, candies, meals, chewing gums, sweeteners, powder to be reconstituted in a liquid, bakeries, cakes, etc.

In one embodiment, the claimed food products and clinical nutrition products are intended for enterally administration or for administration with a device destined to deliver such products directly inside the gastrointestinal tractus without being swallowed.

In one embodiment, at least one betaine and/or one nitric oxide precursor, such as L-arginine present in the food products and clinical nutrition products will be in a slow release and/or controlled release form. The slow release and/or sustained release and/or controlled release forms as described in Inventor's applications referred above, might be preferred; although any other mean to control the release of a betaine and/or one nitric oxide precursor, such as L-arginine, can be used in such food products and clinical nutrition products. The use of such betaines/precursors (of NO) controlled release food products and clinical nutrition products will allow delivering optimally, the claimed compounds and compositions.

In one embodiment the betaines of the invention can be used to treat hereditary and acquired antithrombin deficiency pathologies.

EXAMPLES

Example 1

Induced Focal Cerebral Ischemia on Rats

Experimental Protocol

The aim of this study was to evaluate the activity of Betaine on thrombus formation in a rat model of photochemically-induced brain ischemia. The method (11) is based on local free radical release exerted by filtered light acting on rose Bengal previously injected in animals. Free radicals are known to induce endothelial damage, followed by platelet aggregation, thrombus formation and vascular occlusion. Briefly, an optic fiber in close contact shone denuded intact skulls (diameter of the illuminated circle 5.4 mm, luminance at the entrance of optic fiber was $5.6 \times 10^6$ Ix). After turning on the lamp, an infusion through the caudal vein of a 5 mg/mL (w/v) solution of rose Bengal in saline was started. Two mL of the solution were administered at a flow rate of 0.1 mL/min. After 20 min, at the end of the infusion, the lamp was turned off.

The experimental groups were the followings:

| Groups | Treatments |
|---|---|
| 1 | Saline solution (2.0 mL/kg) sc 1 h before ischemia induction (n = 10) |
| 2 | Acetylsalicylic acid 50 mg/kg iv 30 min before ischemia induction (n = 5) |
| 3 | ASA 200 mg/kg iv 30 min before ischemia induction (n = 10) |

| | 1 Saline (2 mL/kg) | 2 ASA 50 mg/kg | 3 ASA 200 mg/kg | 4 Betaine before induction | 5 Betaine after induction |
|---|---|---|---|---|---|
| n | 10 | 5 | 10 | 10 | 10 |
| Mean | 48 | 35.0 | 40 | 36 | 25 (*) |
| S D | 16 | 9.7 | 20 | 18 | 15 |

| 4 | Betaine 10 mg/kg sc 1 h before ischemia induction (n = 10) |
|---|---|
| 5 | Betaine 10 mg/kg sc at the end of ischemia induction (n = 10) |

Evan's Blue solution (2% w/v) in saline was intravenously injected (1 mL/rat), 18-20 h after the ischemia induction in order to reveal the BBB breakdown. The rats were sacrificed 20 min after Evan's Blue injections and their brains removed. The infarcted area was visually verified, photographed by digital camera and then weighed.

Results

Weight of ischemic area in mg.

Red Ischemic Area ($cm^2$), Excluding Blue Evan Penumbra (*) $P<0,05$

Comments: In this model Betaine showed better efficacy than Aspirin, the reference molecule for stroke treatment. Betaine showed its ability to potently reduce brain injury, as demonstrated in the examples above, which can be measured by determining a reduction in infarct size in the treated versus the control groups. Betaine reduces brain oedemas and by the way alleviates brain injuries. Likewise, functional tests measuring neurological deficits provided further evidence of reduction in brain injury in the treated animals versus the controls. Cerebral blood flow should also be better in the treated animals versus the controls.

In these experiments betaine shows its ability to cross encephalic barrier after being present in blood stream. This crossing capability allied to betaine up-regulating effects on endogenous nitric oxide allows claiming betaine therapeutic uses and benefits in neurodegenerative diseases in general.

Betaine utilisation can be particularly claimed in prevention and treatment in Alzheimer's disease and Parkinson's disease.

| | 1 Saline (2 mL/kg) | 2 ASA 50 mg/kg | 3 ASA 200 mg/kg | 4 Betaine before induction | 5 Betaine after induction |
|---|---|---|---|---|---|
| n | 10 | 5 | 10 | 10 | 10 |
| Mean | 0.35 | 0.322 | 0.29 | 0.335 | 0.28 (*) |
| S D | 0.10 | 0.041 | 0.14 | 0.082 | 0.13 |

According to the experiments, betaine can be particularly efficient when administrated after the stroke or cerebrovascular ischemic event. When transposed to clinical practice, betaines can be particularly efficient in reducing the deleterious symptoms of an ischemic event, particularly a cerebrovascular ischemic event in a patient.

Example 2

Nitric Oxide Production in Healthy Volunteers After Betaine Ingestion

Betaine is administered at 75 mg/kg single oral dose at T0 to fastened healthy volunteers just after the basal blood sample. At T0 and T0+60 mn fresh blood samples are centrifuged to obtain plasma.

The samples are then tested for nitric oxide with the Griess reaction.

|  | status | O.D. | Conc. | Conc. (2) |
|---|---|---|---|---|
| Volunteer 1 | Pre Betaine | 0.144 | 27.19 | 54.37 |
|  | Post | 0.168 | 32.77 | 65.53 |
| Volunteer 2 | Pre | 0.111 | 19.51 | 39.02 |
|  | Post | 0.274 | 57.42 | 114.21 |
| Volunteer 3 | Pre | 0.117 | 20.91 | 41.81 |
|  | Post | 0.178 | 35.09 | 70.19 |
| Volunteer 4 | Pre | 0.116 | 20.67 | 41.35 |
|  | Post | 0.183 | 36.26 | 72.51 |
| Volunteer 5 | Pre | 0.091 | 14.86 | 29.72 |
|  | Post | 0.117 | 20.91 | 41.81 |
| Volunteer 6 | Pre | 0.058 | 7.19 | 14.37 |
|  | Post | 0.079 | 12.07 | 24.14 |

Betaine oral administration markedly increased nitric oxide levels in all tested volunteers. This augmentation occurred uniformly in all tested volunteers and predicts betaine efficiency in NO depletion related pathologies.

Example 3

TEG® Parameters After Betaine Oral Administration in Healthy Volunteers

Betaine is administered at 75 mg/kg single oral dose at T0 to fastened healthy volunteers just after the basal blood sample. At T0 and T0+60 mn the fresh blood samples are immediately evaluated in the Thromboelastograph (TEG®—Haemoscope Corp.—Illinois).

|  |  | R (mn) | K (mn) | MA (mm) | α Angle (°) |
|---|---|---|---|---|---|
| Volunteer 1 | Basal value | 2.5 | 2.2 | 66.6 | 66.1 |
|  | T0 + 60 mn | 4.8 | 1.3 | 65.8 | 71.9 |
| Volunteer 2 | Basal value | 5.6 | 1.9 | 61.3 | 62.5 |
|  | T0 + 60 mn | 8.4 | 2.7 | 61.9 | 66.9 |
| Volunteer 3 | Basal value | 3.7 | 1.2 | 64.3 | 74.9 |
|  | T0 + 60 mn | 6.3 | 1.3 | 70.1 | 70.4 |
| Volunteer 4 | Basal value | 4.3 | 3.8 | 54.6 | 54.2 |
|  | T0 + 60 mn | 5.8 | 2.5 | 52.6 | 57.5 |
| Volunteer 5 | Basal value | 6.0 | 1.5 | 64.9 | 67.8 |
|  | T0 + 60 mn | 7.3 | 1.8 | 65.0 | 65.5 |
| Volunteer 6 | Basal value | 6.3 | 1.8 | 50.0 | 67.1 |
|  | T0 + 60 mn | 7.4 | 2.0 | 56.8 | 64.2 |
| Mean + | Basal value | 4.7 | 2.1 | 60.3 | 65.4 |
| Deviation | T0 + 60 mn | 6.8 | 1.9 | 62.0 | 66.1 |
|  | Δ | +45% | −8% | +3% | +1% |

Comments

R parameter corresponds to rate of initial fibrin formation, and is functionally related to plasma clotting factors and clot formation. Betaine significantly prolonged healthy volunteers' blood coagulation 60 minutes after oral administration. This effect on R prolongation occurred uniformly in tested volunteers and was as potent as Lovenox® anticoagulation in post orthopaedic surgery patients when evaluated with TEG®. The other parameters remained stable which could explain betaine antithrombotic effect without affecting bleeding

Example 4

Examples of Nutritional Compositions:

For Cystic Fibrosis, an inherited disease,

Glycine betaine has been added to the following products marketed by NUMICO: Scandishake Mix, Calogen, Duocal, Maxijul, Solagen, Emsogen and Liquigen.

The amount of glycine betaine added was adapted for having a final betaine concentration in the nutritional compositions respectively of 1% by weight, 2% by weight, 5% by weight, 10% by weight, and 20% by weight.

Chronic Obstructive Pulmonary Disease

Glycine betaine has been added to Respifor sold by Numico. The amount of glycine betaine added was adapted for having a final betaine concentration in the nutritional compositions respectively of 1% by weight, 2% by weight, 5% by weight, 10% by weight, and 20% by weight.

Woundcare

Glycine betaine has been added to Cubitan and Cubison sold by Numico.

The amount of glycine betaine added was adapted for having a final betaine concentration in the nutritional compositions respectively of 1% by weight, 2% by weight, 5% by weight, 10% by weight, and 20% by weight.

Dysphagia

Glycine betaine has been added to Fortimel, Fortijuice/Ensini, Nutridrink/Fortisip, Fortifresh products, nutriment powders such as Polycal/Fantomalt and Protifar adapted to be incorporated into foods and drinks are also a useful choice. (Products sold by Numico).

The amount of glycine betaine added was adapted for having a final betaine concentration in the nutritional compositions respectively of 1% by weight, 2% by weight, 5% by weight, 10% by weight, and 20% by weight.

Diabetes Mellitus

Glycine betaine has been added to Diasip and Diason sold by Numico.

The amount of glycine betaine added was adapted for having a final betaine concentration in the nutritional compositions respectively of 1% by weight, 2% by weight, 5% by weight, 10% by weight, and 20% by weight.

Renal Disease

Glycine betaine has been added to Renilon drink, Kindergen, Dialamine, Maxisorb, Super Soluble Maxipro, Maxijul LE and Calogen, sold by Numico, The amount of glycine betaine added was adapted for having a final betaine concentration in the nutritional compositions respectively of 1% by weight, 2% by weight, 5% by weight, 10% by weight, and 20% by weight.

Perioperative

Glycine betaine has been added to Nutricia Preop sold by Numico.

The amount of glycine betaine added was adapted for having a final betaine concentration in the nutritional compositions respectively of 1% by weight, 2% by weight, 5% by weight, 10% by weight, and 20% by weight.

Example 5

Nitric Oxide Production and Tissue Factor Pathway Inhibitor (TFPI) in Healthy Volunteers After Betaine Ingestion After obtaining the baseline blood samples (sample a) from fastened normal healthy volunteers (n=10), Betaine was repeatedly administered in daily doses of 6 g. (2×3) for 1 week. After obtaining the 1 week blood sample from fastened volunteers (sample b) Betaine was again administered orally at a dose of 3 g. and a third blood sample drawn after one hour (sample c). Each time the blood was drawn TEG was also performed which exhibited marked prolongation of the reaction time, i.e. rate of initial fibrin formation, compared to the baseline values confirming its anticoagulant property. The blood samples were centrifuged and the separated platelet poor plasma was then aliquoted and frozen at −70° C. for subsequent analysis for nitric oxide (NO), tissue factor pathway inhibitor (TFPI) activity levels and global clotting assays. The total nitric oxide is determined based on the enzymatic conversion of nitrate to nitrite by nitrate reductase and colorimetric detection of nitrite as an azo dye product of the Griess reaction (R & D Systems Inc., Minneapolis Minn.) and the TFPI activity measured (American Diagnostica (Stamford, Conn.) exhibited significant increase and are mentioned in the tables below.

The samples are identified for each donor as number of donor (1, 2, etc) followed by the letter of the sample (a, b, c).

TFPI Activity and TFPI Concentration Plasma Levels

|  | ACTIVITY | | CONCENTRATION | |  |
| --- | --- | --- | --- | --- | --- |
| Sample | O.D. | U/ml | ng/ml | O.D. | ng/ml |
| 1 a | 0.383 | 2.12 | 116.40 | 0.954 | 58.00 |
| 1 b | 0.265 | 3.52 | 193.76 | 1.132 | 70.31 |
| 1 c | 0.27 | 3.45 | 189.62 | 1.03 | 63.25 |
| 2 a | 0.332 | 2.64 | 145.08 | 1.27 | 79.85 |
| 2 b | 0.212 | 4.43 | 243.59 | 1.414 | 89.81 |
| 2 c | 0.234 | 4.03 | 221.52 | 1.321 | 83.38 |
| 3 a | 0.369 | 2.25 | 123.66 | 1.075 | 66.37 |
| 3 b | 0.28 | 3.30 | 181.61 | 0.975 | 59.45 |
| 3 c | 0.26 | 3.60 | 197.99 | 1.373 | 86.98 |
| 4 a | 0.399 | 1.98 | 108.63 | 0.784 | 46.24 |
| 4 b | 0.323 | 2.74 | 150.83 | 1.073 | 66.23 |
| 4 c | 0.375 | 2.19 | 120.49 | 1.133 | 70.38 |
| 5 a | 0.456 | 1.54 | 84.93 | 1.614 | 103.65 |
| 5 b | 0.33 | 2.66 | 146.34 | 1.335 | 84.35 |
| 5 c | 0.432 | 1.71 | 94.20 | 1.216 | 76.12 |
| 6 a | 0.386 | 2.09 | 114.90 | 0.794 | 46.93 |
| 6 b | 0.364 | 2.30 | 126.36 | 0.797 | 47.14 |
| 6 c | 0.323 | 2.74 | 150.83 | 1.135 | 70.52 |
| 7 a | 0.418 | 1.82 | 100.07 | 1.076 | 66.44 |
| 7 b | 0.377 | 2.17 | 119.46 | 1.049 | 64.57 |
| 7 c | 0.304 | 2.98 | 163.73 | 1.31 | 82.62 |
| 8 a | 0.325 | 2.72 | 149.53 | 0.995 | 60.83 |
| 8 b | 0.2 | 4.66 | 256.55 | 1.22 | 76.40 |
| 8 c | 0.207 | 4.53 | 248.91 | 1.405 | 89.19 |
| 9 a | 0.253 | 3.71 | 204.07 | 1.195 | 74.67 |
| 9 b | 0.274 | 3.39 | 186.37 | 1.465 | 93.34 |
| 9 c | 0.257 | 3.65 | 200.57 | 1.384 | 87.74 |
| 10 a | 0.248 | 3.79 | 208.52 | 1.435 | 91.27 |
| 10 b | 0.303 | 2.99 | 164.44 | 0.799 | 47.28 |
| 10 c | 0.285 | 3.23 | 177.73 | 0.963 | 58.62 |

Nitric Oxide Plasma Levels

| Samples | OD | Conc | Conc (×2) |
| --- | --- | --- | --- |
| 1 a | 0.12 | 21.5 | 43 |
| 1 b | 0.12 | 21.5 | 43 |
| 1 c | 0.165 | 31.28 | 62.565 |
| 2 a | 0.082 | 13.24 | 26.478 |
| 2 b | 0.132 | 24.11 | 48.217 |
| 2 c | 0.146 | 27.15 | 54.304 |
| 3 a | 0.094 | 15.85 | 31.696 |
| 3 b | 0.086 | 14.11 | 28.217 |
| 3 c | 0.088 | 14.54 | 29.087 |
| 4 a | 0.137 | 25.2 | 50.391 |
| 4 b | 0.155 | 29.11 | 58.217 |
| 4 c | 0.21 | 41.07 | 82.13 |
| 5 a | 0.129 | 23.46 | 46.913 |
| 5 b | 0.154 | 28.89 | 57.783 |
| 5 c | 0.205 | 39.96 | 79.957 |
| 6 a | 0.071 | 10.85 | 21.696 |
| 6 b | 0.063 | 9.11 | 18.217 |
| 6 c | 0.149 | 27.8 | 55.609 |
| 7 a | 0.122 | 21.93 | 43.87 |
| 7 b | 0.142 | 26.28 | 52.565 |
| 7 c | 0.144 | 26.72 | 53.435 |
| 8 a | 0.073 | 11.28 | 22.565 |
| 8 b | 0.114 | 20.2 | 40.391 |
| 8 c | 0.126 | 22.8 | 45.609 |
| 9 a | 0.093 | 15.63 | 31.261 |
| 9 b | 0.125 | 22.59 | 45.174 |
| 9 c | 0.14 | 25.85 | 51.696 |
| 10 a | 0.086 | 14.11 | 28.217 |
| 10 b | 0.082 | 13.24 | 26.478 |
| 10 c | 0.076 | 11.93 | 23.87 |

Comments:

Both Nitric oxide levels as TFPI activity and TFPI concentration plasma levels are increased by betaine oral administration. This double, even triple activity constitutes a unique pharmacological profile and property in the medicinal world. Based on these particularity betaine can be claimed to be beneficial in the pathologies where either NO and/or TFPI (i.e. tissue factor) are involved. Accordingly, the betaines of the invention are claimed to have a simultaneous up regulating actions either on constitutive NO or on TFPI. On the other hand these results clearly show the anticoagulant (TFPI) and the antiaggregant (NO) simultaneous and synergically pharmacological properties of betaines. Additionally TFPI possess antiinflammatory activities, thus the betaines of the invention by augmenting both immunological and functional (activity) TFPI claim simultaneous antiaggregant, antiinflammatory and anticoagulant activities in a mammal and/or in a patient in need.

Example 6

Betaine Effects on Patients Affected by Pulmonary Hypertension

Nine patients suffering from Pulmonary Arterial Hypertension and taking 125 mg Bosentan bid were randomly assigned to placebo (lactose monohydrate) 6 g/day bid (4 patients) or to anhydrous betaine 6 g/day bid (5 patients) during two weeks. They were assessed for haemodynamic variables and for 6 minutes walking test at inclusion and after the two weeks of medication with placebo or betaine. Pulmonary Artery Pressure (PAP) and Heart rate were non-invasively estimated by Doppler echocardiography method. 6MWT was performed on a treadmill.

The study was approved by the Ethical Committee of University Hospital of Padova, Italy.

The results of the study are given in the table below:

| patients | Week 0 ECO 0 PAP | Week 2 ECO 2 PAP | Heart rate 0 | Heart rate 2 | 6MWT 0 | 6MWT 2 |
| --- | --- | --- | --- | --- | --- | --- |
| Patients on Betaine | | | | | | |
| #1 | 70 | 60 | 70 | 67 | 514 | 504 |
| #2 | 86 | 80 | 117 | 74 | 340 | 360 |
| #3 | 107 | 65 | 78 | 69 | 426 | 411 |
| #4 | 65 | 58 | 66 | 72 | 406 | 410 |
| #5 | 84 | 71 | 85 | 84 | 360 | 380 |
| mean | 82.4 | 66.8 | 83.2 | 73.2 | 409.2 | 413 |
| Patients on Placebo | | | | | | |
| #6 | 75 | 75 | 65 | 70 | (468) | (–) |
| #7 | 55 | 57 | 60 | 78 | 438 | 402 |
| #8 | 36 | 30 | 106 | 78 | 524 | 566 |
| #9 | 70 | 77 | 92 | 80 | 195 | 192 |
| mean | 59 | 59.75 | 80.75 | 76.5 | 385.67 | 386.67 |

Comments: Patients on Bosentan+ placebo did not show any amelioration on the tested variables after the 2 weeks of treatments, comparatively to basal values. One patient on placebo (#6) was not able to perform the 6 minutes walking test at the second visit, its basal value for 6MWT was not taken in account in the mean values.

On the contrary, the patients on Bosentan+Betaine showed a very significant drop in Pulmonary Arterial Pressure (PAP) from a mean of 82.4 mmHg to a mean of 66.8 mmHg. This 15.6 mmHg drop is quite significant and shows Betaine effectiveness when being added to the dual endothelin antagonist Bosentan on an essential marker of Pulmonary Arterial Hypertension disease. Similarly, the effect of the combination therapy of Bosentan+ Betaine showed a very significant drop in Heart rate of 10 beats/minute.

Two weeks are a too short period of time to see changes in 6MWT, which slightly but no significantly was ameliorated (+4m). But, based on the important changes in PAP and Heart rate it is expected that significant changes may happen on longer period of time of active treatment.

None of the patients dropped out of the study and no undesired effects were noted in the patients on Bosentan+ Betaine$_1$ which is quite unusual in other therapies combining endothelin antagonists (such as Bosentan) with other medicines (e.g. Sildenafil, etc.).

These results show the beneficial effects of Betaine which is suitable and may be efficient in all the diseases induced by pathological expressions of endothelin and/or constitutive nitric oxide depletion or low levels. Betaine pharmacological effects are related to its enhancing effects of endogenous or constitutive Nitric Oxide production and/or production pathway i.e. on constitutive or endogenous nitric oxide synthase expressions.

Hence, betaine treatment alone or when being added to conventional treatment of Pulmonary Hypertension may represent a true benefit for Pulmonary Hypertension patients, when providing more effective treatment for ameliorating relevant clinical markers such as PAP, heart rhythm and treadmill walking performance, while preserving and/or ameliorating patients' safety, quality of life and survival.

Example 7

Preamble

Clinical trials of several COX-2 selective and non-selective NSAIDs of up to three years duration have shown an increased risk of serious cardiovascular (CV) thrombotic events, myocardial infarction, and stroke, which can be fatal. All NSAIDS, both COX-2 selective and non-selective, may have a similar risk. Patients with known CV disease or risk factors for CV disease may be at greater risk. To minimize the potential risk for an adverse CV event in patients treated with an NSAID, the lowest effective dose should be used for the shortest duration possible but in certain situations longer medication is necessary exposing patients to life threatening cardiovascular events. It is a further goal of the present application to provide safer and more efficient pharmaceutical combinations and/or dosage forms and/or co-administrations and/or methods of treatments comprising of one or more betaine and one or more non selective COX 2 inhibitor and/or one or more selective COX 2 inhibitor.

Animal Experiments

Male Wistar rats (200-270 gram) were used for the experiments. The rats were anaesthetized by intramuscular injection (250 mgkg b.m.) of Thiopental sodium (Nesdonal, Laboratoire Specia, France). After the medial laparotomy the intestinal loop was placed on the microscope table. Vascular lesions were produced by Argon laser Principle of laser-induced thrombosis (Seiffge D. et al., 1989; Weichter W. et al., 1983)

In this model, a laser beam is targeted to the mesenteric circulation of the rat, in veinules or arterioles (15 to 30 microns diameter). This shot causes a well limited lesion of the vascular endothelium (only few cells are destroyed) exposing the thrombogenetic under-layer of the sub-endothelium. The contact of blood with this surface triggers the adherence of platelets via glycoproteins Ib & IIb IIIa. This adherence of platelets is followed by their activation: they form pseudopods and secrete the content of their granules. As a consequence thrombus formation occurs within few seconds. This platelet rich thrombus rapidly enlarges under influence of blood flow, embolises (i.e. is disrupted and carried by the flow from the thrombogenic area) before a new thrombus being formed again on the injured surface.

The vessel is observed for 60 sec, and if no emboli are formed another laser shot is fired. Up to four shots can be fired if no emboli (platelet thrombus) are readily appearing. The number of successive laser beams and emboli formed are then recorded.

In the presence of an antithrombotic compound a higher number of laser shots are necessary to induce thrombus formation. Similarly, a smaller number of emboli (platelet thrombi) are formed as compared with controls and the duration of the embolisation is also shorter.

In presence of prothrombotic compounds, such as COX 2 inhibitors, less laser shots are necessary to induce thrombus formation. Similarly, a higher number of emboli (platelet thrombi) are formed as compared with controls and the duration of the embolisation is also longer.

The avoidance of chemical or mechanical agents to trigger thrombosis makes this physiological model highly relevant. Actually it closely mimics situations where the vascular tunica is injured after atherosclerotic plaque rupture followed by thrombus formation and vessel occlusion. The presence or administration of prothrombotic compound enhances such thrombotic response leading to a higher number of formed clots (emboli). In clinical situation that would mean that patients taking COX 2 inhibitors are at much higher risk to have cardiovascular events.

Induced Bleeding Time IBT (E. Dejana. Bleeding time in rats. Thrombosis Research. 1982)

At the end of the laser experiments, the tails of anaesthetised rats are dipped for 5 minutes in a 37° C. water bath so as to provoke dilatation of the peripheral vessels. The tails are then removed and cut at the tip (~8 mm), the chronometer being started The tails are positioned to lean vertically allowing the blood loss to freely flow down. The IBT is defined as being the time period comprised between the tail transection and the end of the bleeding. The end of bleeding is defined as the time when the last drop of blood fall from the tail and no other drop fall for the next 180 seconds.

Whole Blood Aggregation Tests

The whole blood aggregation is made in accordance to the methods described by Cardinal D C, Flower R J. The electronic aggregometer: a novel device for assessing platelet behavior in blood. J Pharm Meth 1980; 3: 135-58 and by Sweeney J D. Whole Blood aggregometry. American Journal of Clinical Pathology, December 1989; 92(6):794-7.

Blood is sampled by intracardiac puncture on trisodium citrate solution (3, 8% sodium citrate/blood 1/9 vv) using the 2 syringes technique.

ADP 5 µM in final concentration is used as agonist. Amplitudes are expressed in ohms ($\Omega$) and velocities in ohm/min ($\Omega$/min)

Substances Administrations & Dosages

Betaine is orally administrated to animals at 50 mg/kg, 60 minutes before laser thrombosis. Similarly the selective COX 2 inhibitors are orally administrated simultaneously with betaine to animals 60 minutes before laser thrombosis.

Results

| | laser beams | emboli | duration of embolisation | amplitude | velocity | bleeding time |
|---|---|---|---|---|---|---|
| Saline control | | | | | | |
| rat 1 | 2 | 4 | 2 | 11 | 9 | 125 |
| rat 2 | 2 | 6 | 3 | 9 | 7 | 135 |
| rat 3 | 2 | 6 | 3 | 14 | 12 | 105 |
| rat 4 | 1 | 7 | 4 | 11 | 9 | 90 |
| rat 5 | 1 | 6 | 3 | 8 | 9 | 115 |
| rat 6 | 2 | 6 | 2 | 14 | 7 | 125 |
| Mean | 1.67 | 5.83 | 2.83 | 11.17 | 8.83 | 115.83 |
| Celebrex ® 10 mg + saline | | | | | | |
| rat 1 | 2 | 9 | 4 | 13 | 8 | 150 |
| rat 2 | 1 | 8 | 4 | 12 | 7 | 125 |
| rat 3 | 2 | 11 | 5 | 14 | 7 | 125 |
| rat 4 | 1 | 17 | 9 | 21 | 13 | 90 |
| rat 5 | 1 | 11 | 5 | 13 | 9 | 105 |
| rat 6 | 2 | 12 | 5 | 13 | 8 | 95 |
| Mean | 1.5 | 11.33 | 5.33 | 14.33 | 8.67 | 115 |
| Celebrex ® 10 mg + Betaine 50 mg | | | | | | |
| rat 1 | 2 | 6 | 2 | 13 | 9 | 110 |
| rat 2 | 1 | 7 | 3 | 12 | 7 | 115 |
| rat 3 | 2 | 6 | 3 | 11 | 8 | 100 |
| rat 4 | 2 | 5 | 2 | 10 | 7 | 135 |
| rat 5 | 3 | 4 | 2 | 7 | 3 | 105 |
| rat 6 | 3 | 6 | 2 | 5 | 7 | 115 |
| Mean | 2.17 | 5.67 | 2.33 | 9.67 | 6.83 | 113.33 |
| NS 398 selective COX2 Inhibitor 5 mg + saline | | | | | | |
| rat 1 | 2 | 11 | 5 | 9 | 9 | 215 |
| rat 2 | 2 | 9 | 4 | 10 | 7 | 240 |
| rat 3 | 1 | 10 | 5 | 2 | 7 | 130 |
| rat 4 | 2 | 9 | 4 | 12 | 7 | 115 |
| rat 5 | 2 | 7 | 3 | 6 | 7 | 180 |
| rat 6 | 2 | 8 | 2 | 9 | 5 | 210 |
| Mean | 1.83 | 9 | 3 | 8 | 7 | 181.67 |
| NS 398 selective COX2 Inhibitor 5 mg + 50 mg Betaine | | | | | | |
| rat 1 | 2 | 7 | 3 | 9 | 9 | 125 |
| rat 2 | 2 | 5 | 3 | 8 | 7 | 115 |
| rat 3 | 2 | 4 | 2 | 9 | 7 | 120 |
| rat 4 | 1 | 7 | 3 | 8 | 3 | 115 |
| rat 5 | 2 | 6 | 2 | 11 | 8 | 135 |
| rat 6 | 1 | 5 | 2 | 10 | 7 | 100 |
| Mean | 1.67 | 5.67 | 2.5 | 9.17 | 6.83 | 118.33 |

Betaine administration clearly protects animals from selective COX 2 inhibitors thrombogenicity. Betaine co-administration clearly normalise the number of laser beams, number of emboli and duration of embolisation to the saline control values. Bleeding time and whole blood aggregation are not or slightly affected and remain either with selective COX 2 inhibitors alone or in combination with betaine within or slightly higher than saline control values.

That means that selective COX 2 inhibitors in combination with betaine can be safely prescribed to patients in need without compromising their vascular outcome. Moreover, according to the invention, the anti-adhesive and anti-inflammatory properties of betaines will allow to lower the needed dose of selective COX 2 inhibitors for obtaining the pharmacological efficiency in inflammatory diseases.

Hence, the invention also claims a pharmaceutical combination comprising one or more betaine and one or more selective COX 2 inhibitor.

The invention also claims a method of treatment of a mammal in which the patient is administered with an efficient therapeutical amount of betaine and an efficient therapeutical amount of one or more selective COX 2 inhibitor.

The combinations of the invention can be particularly beneficial in patients suffering of Hepatic Insufficiency and/or Renal Insufficiency.

The combinations of the invention can be particularly beneficial in patients for the treatment of peri-operative pain in the setting of coronary artery bypass graft (CABG) surgery.

The combinations of the invention can be particularly beneficial to prevent or alleviate one or more side effect selected from Cardiovascular Events, Cardiovascular Thrombotic Events, cerebrovascular events, stoke, bleeding, Hypertension, Congestive Heart Failure and Oedema, Gastrointestinal Effects, Risk of Ulceration, Bleeding and Perforation, Anaphylactic Reactions, Skin Reactions, Haematological Effects, Anaemia and Asthma.

In limited clinical situations the combinations of the invention have shown at least 10% higher therapeutical efficiency than the antiinflammatory compound alone. Improvement in several patients treated for rheumatoid arthritis was noticed by a reduction in joint swelling, a reduction in duration of morning stiffness, a reduction in disease activity as assessed by both the investigator and patient, and by increased mobility as demonstrated by a reduction in walking time.

The application claims a pharmaceutical combination and/or a method of treatment for treating one or more trouble selected from inflammation, arthritis, Rheumatoid arthritis, Osteoarthritis, pain, Alzheimer's/low back pain said combination comprising one or more antiinflammatory agent and one or more betaine wherein the betaine is in an amount of at least 5 times the amount of the selective COX 2 inhibitor and/or wherein the betaine is in an amount of at least 5 times the amount of the non selective COX 2 inhibitor.

The application claims a pharmaceutical combination comprising at least:
  A first compound selected among the group consisting of NSAID, non selective COX inhibitors, selective COX 2 inhibitors, and pharmaceutical derivatives and combinations thereof, and
  A second compound selected from the group consisting of lipidic betaines, betaines lipids, betaine of formula $(CH_3)_3N^+(CH_2)_nCOO^-$ with n an integer from 1 to 5, pharmaceutically acceptable salts thereof, esters thereof, precursors thereof, and mixtures thereof with the provision that said second compound is different from the first compound and in which the amount of second compound (i.e. one or more betaine) is at least 5 times the amount calculated as the first compound weight, of said first compound.

The ratio of 5 for the betaine compound is adopted since lower ratios than 5 calculated as second compound weight/first compound weight (betaine/NSAID) have shown to be not or less effective in enhancing first compound pharmacological effects and/or lessening first compound side effects. For example in animals, betaine counteract naproxen tail cut bleeding at 5/1 ratio (betaine/naproxen) but not at 1/1, 2/1 or 3/1 ratios as demonstrated in rat bleeding times. In the same manner, betaine enhanced naproxen pharmacological antiinflammatory activity optimally since ratio of 5 but not at 1/1 or 2/1 ratios. At 1/1 and 21:1 ratios (betaine/naproxen) naproxen induced thrombocytopenia in rats was not counteracted but efficiently at 5/1 ratio (betaine/naproxen) as demonstrated by platelet count in animals.

According to the invention the one or more selective COX 2 inhibitor can be selected from the group consisting of: Celecoxib, Valdecoxib, Rofecoxib, etoricoxib, lumiracoxib, parecoxib, their acceptable salts and theirs combinations.

The ratios of the combinations betaines/selective COX 2 inhibitors can vary between 5 to 300, wherein the daily dosage of betaine can be comprised between 2 and 12 grams and the daily dosage of the non selective COX 2 inhibitor can vary between 10 and 500 mg daily depending on the particular daily authorized dose of each non selective COX 2 inhibitor as defined and described in the websites of US Food and Drug Administration (FDA), European Agency for the Evaluation of Medicinal Products (EMEA) or http://www.rxlist.com/ as the case may be.

The pharmaceutical combinations and/or dosage forms and/or co-administrations and/or methods of treatments of one or more betaine and one or more selective COX 2 inhibitor will permit to lower the daily authorized dose of the one or more non selective COX 2 inhibitor advantageously by 10%, preferably by 20%, more preferably by 30%, more preferably by 40%, specifically by 50%, more specifically by 60%.

According to the invention the one or more non selective COX 2 inhibitor can be selected from the group consisting of:
Tolmetin, Sulindac, Salsalate Piroxicam, Oxaprozin, Naproxen, Naprosyn, Nabumetone, Meloxicam Mefenamic Acid, Ketoprofen, Indomethacin, Diflunisal, Diclofenac, Etodolac, Fenoprofen, Flurbiprofen, Ibuprofen, their acceptable salts and theirs combinations.

The ratios of the combinations betaines/non selective COX 2 inhibitors can vary between 5 to 300, wherein the daily dosage of betaine can be comprised between 2 and 12 grams and the daily dosage of the non selective COX 2 inhibitor can vary between 15 and 1500 mg daily depending on the particular daily authorized dose of each non selective COX 2 inhibitor as defined and described in the websites of US Food and Drug Administration (FDA), European Agency for the Evaluation of Medicinal Products (EMEA) or http://www.rxlist.com/ as the case may be.

The pharmaceutical combinations and/or dosage forms and/or co-administrations and/or methods of treatments of one or more betaine and one or more non selective COX 2 inhibitor will permit to lower the daily authorized dose of the one or more non selective COX 2 inhibitor advantageously by 10%, preferably by 20%, more preferably by 30%, more preferably by 40%, specifically by 50%, more specifically by 60%.

The pharmaceutical combinations and/or dosage forms and/or co-administrations and/or methods of treatments of one or more betaine and one or more non selective COX 2 inhibitor and/or one or more selective COX 2 inhibitor can be suitable for example for different routes of administration. For example all the administration forms and/or routes known and applied in clinical settings can be used according to the present invention. Such routes including, but not limited to, oral, dermal, transdermal, subcutaneous, parenteral, intraperitoneal, sublingual, nasal, pulmonary, rectal and theirs combinations. The present invention includes all such methods of administration. The combination therapy is especially efficacious on conditions associated with inflammation.

Examples of administration forms are: tablets, capsules, patches, injectable forms, releasing forms, sublingual administration form, powders (for example for inhalation therapy, buccal inhalation), syrup, solution (nebulization, for example for inhalation therapy, buccal inhalation), subcutaneous injectable dosage forms, injectable dosage forms, patches (to be applied on the skin), entero soluble oral dosage forms, gastro insoluble tablets or capsules, provided with an entero soluble coating or matrix or system and slow release dosages forms.

The invention is also disclosed in the attached claims, the content of which is incorporated in the present specification,

The invention claimed is:

1. A method for treating a patient suffering from a condition related to constitutive nitric oxide deficiency, wherein said condition is pulmonary hypertension, said method comprising the step of administering to the patient an efficient therapeutical amount of betaine for increasing in said patient at least one nitric oxide production pathway selected from the group consisting of constitutive nitric oxide synthase expression, constitutive Endothelial nitric oxide synthase expression, eNOS nitric oxide synthase expression, neural NOS nitric oxide synthase expression (nNOS), platelet NOS nitric oxide synthase expression, cNOS nitric oxide synthase expression, Type III nitric oxide synthase expressions, calcium dependant nitric oxide synthase expression, calcium dependant nitric oxide synthase production, endogenous nitric oxide production, and combinations thereof, said betaine being administered orally in an oral composition comprising at least (a) 20% by weight betaine and (b) 20% by weight L-arginine or a physiologically acceptable salt thereof.

2. The method of claim 1, in which the patient is administered with an efficient therapeutical amount of glycine betaine for increasing the rate of said at least one nitric oxide production pathway in said patient.

3. The method of claim 1, in which the patient is administered with an efficient therapeutical amount of glycine betaine for increasing by a factor comprised between 1.2 and 3 the rate of said at least one nitric oxide production in said patient.

4. The method of claim 1, in which the weight ratio L-arginine or salt thereof/betaine is comprised between 0.5 and 2.

5. The method of claim 1 for treating a patient suffering from a condition related to deficiency of nitric oxide, wherein said condition is pulmonary hypertension, in which the patient is administered with an efficient therapeutical amount of betaine for increasing bioavailability of endothelial nitric oxide in a mammal.

6. The method of claim 1 for treating a patient suffering from a condition related to deficiency of nitric oxide, wherein said condition is pulmonary hypertension, in which the patient is administered with an efficient therapeutical amount of betaine for controlling and/or up-regulating endothelial nitric oxide bioavailability in a mammal.

7. The method of claim 1 for treating a patient suffering from a condition related to deficiency of nitric oxide, wherein said condition is pulmonary hypertension, in which the patient is administered with an efficient therapeutical amount of betaine for controlling and/or up-regulating endogenous nitric oxide synthase expression in a mammal.

8. The method of claim 1, in which the patient is further administered a therapeutical effective amount of at least one compound selected from the group consisting of nifepidine, arginine analogues, stimulators of NO release, carbachol, acetylcholine, bradykinin and combinations thereof.

9. The method of claim 1, in which the patient is further administered a therapeutical effective amount of at least one compound selected from the group consisting of statins, probucol, antioxidant vitamins, eNOS substrate, cofactors thereof, tetrahydrobiopterin, and combinations thereof.

10. The method of claim 1, in which the patient is further administered an effective amount of at least one active agent selected from the group consisting of natural antioxidants, vitamins C, ascorbic acid, vitamins E, tocopherol isomers, a-tocopherol, tocotrienols, vitamin E isomers, probucol, ascorbate, phytochemicals, flavonoids, isoflavones, polyphenols, anthocyans, and combinations thereof.

11. The method of claim 1, in which the patient is further administered a therapeutical effective amount of bosentan.

12. A method for treating a patient suffering from a condition related to excess endothelin-1 (ET-1), in which the patient is administered with an efficient therapeutical amount of betaine for lowering endothelin-1 (ET-1) levels in said patient, wherein said condition is pulmonary hypertension.

13. The method of claim 12, in which the patient is administered with an efficient therapeutical amount of glycine betaine for decreasing the rate of endothelin-1 (ET-1) expression in said patient.

14. The method of claim 12, in which the patient is administered with an efficient therapeutical amount of glycine betaine for decreasing by a factor of between 1.2 and 5 the rate of endothelin-1 (ET-1) expression in said patient.

15. The method of claim 12, in which the patient is further administered a therapeutical effective amount of bosentan.

16. The method of claim 12, in which a clinical marker for pulmonary hypertension is improved in the patient, said clinical marker being selected from the group consisting of pulmonary arterial pressure, heart rhythm, 6 minute walking test performance on a treadmill, quality of life, and survival.

17. A method for treating a patient suffering from a condition related to endothelial cells, in which said patient is administered an efficient therapeutical amount of betaine for improving endothelial cell function through activation of eNOS and through protection of the endothelium from oxidative stress, wherein said condition is pulmonary hypertension.

18. The method of claim 17, in which the patient is further administered a therapeutical effective amount of bosentan.

19. A method for treating a patient suffering from a condition related to lack of activated eNOS, in which said patient is administered an efficient therapeutical amount of betaine to destabilize the complex between eNOS and caveolin for activating eNOS, wherein said condition is pulmonary hypertension.

20. The method of claim 19, in which the patient is further administered a therapeutical effective amount of bosentan.

21. A method for increasing constitutive Nitric Oxide Synthase activity in a subject to treat a condition favorably affected by an increase in constitutive Nitric Oxide levels in a cell, a tissue, an organ, a bodily fluid, blood, comprising: administering to a subject in need of such treatment an effective amount of a betaine; and co-administering a substrate of Nitric Oxide Synthase, wherein said condition is pulmonary hypertension.

22. The method of claim 21, in which the patient is further administered a therapeutical effective amount of bosentan.

* * * * *